US012664307B1

(12) United States Patent
Lee

(10) Patent No.: US 12,664,307 B1
(45) Date of Patent: Jun. 23, 2026

(54) BEDSIDE AI PERMIT-BEFORE-FINALIZATION GATE AND SAFETY RECEIPT RAIL FOR CLINICAL EDGE INFERENCE

(71) Applicant: Yong Bok Lee, Sheridan, WY (US)

(72) Inventor: Yong Bok Lee, Sheridan, WY (US)

(73) Assignee: Light & Salt LLC, Sheridan, WY (US)

( * ) Notice: Subject to any disclaimer, the term of this patent is extended or adjusted under 35 U.S.C. 154(b) by 0 days.

(21) Appl. No.: 19/442,781

(22) Filed: Jan. 7, 2026

Related U.S. Application Data

(60) Provisional application No. 63/932,297, filed on Dec. 5, 2025.

(51) Int. Cl.
G06F 21/62 (2013.01)
G06F 21/60 (2013.01)
G16H 40/60 (2018.01)
H04L 9/40 (2022.01)

(52) U.S. Cl.
CPC ........ *G06F 21/6245* (2013.01); *G06F 21/604* (2013.01); *G16H 40/60* (2018.01); *H04L 63/10* (2013.01); *G06F 2221/2141* (2013.01)

(58) Field of Classification Search
None
See application file for complete search history.

(56) References Cited

U.S. PATENT DOCUMENTS 8,051,459 B2 11/2011 Zhang et al.
8,220,029 B2 7/2012 Zhang et al.

8,321,353 B2 11/2012 Hamid et al.
8,370,646 B2 2/2013 Nason et al.
8,555,072 B2 10/2013 Camenisch et al.
8,677,453 B2 3/2014 Chang et al.
8,832,778 B2 9/2014 McCune et al.
8,959,580 B2 2/2015 Lim
9,083,746 B2 7/2015 Hamid
(Continued)

OTHER PUBLICATIONS

Oasis, "eXtensible Access Control Markup Language (XACML) Version 3.0—Core Specification," Oasis Standard, Jan. 22, 2013.
(Continued)

*Primary Examiner* — Michael Pyzocha

(57) ABSTRACT

Systems and methods govern bedside AI inference output finalization on a clinical device. A permit rail intercepts an inference request or a user-interface finalization request for an inference episode, obtains an attested device-state vector, a clinical context envelope, and a clinician identity token, and evaluates a policy graph to compute a permit outcome as a permit value or a non-permit value. A user-interface finalization gate at a commit boundary prevents finalization unless the permit outcome corresponds to the permit value; in certain embodiments, an override indicator or attestation satisfying policy is received and incorporated into policy evaluation. For each episode, the device generates a structured bedside safety receipt encoding the device-state vector, clinical context envelope, clinician identity token, policy identifier and version/digest/epoch information, the permit outcome, and an output summary or digest, and may include finalization provenance and integrity protection, including a digital signature or tamper-evident anchoring commitment.

20 Claims, 5 Drawing Sheets

(56)  References Cited

U.S. PATENT DOCUMENTS

| | | | |
|---|---|---|---|
| 9,237,155 | B1 | 1/2016 | Cavage et al. |
| 10,685,140 | B2 | 6/2020 | Barday et al. |
| 11,108,559 | B2 | 8/2021 | Resch et al. |
| 11,362,897 | B2 | 6/2022 | Schirmer et al. |
| 12,464,027 | B2 | 11/2025 | Arkoff et al. |
| 2015/0066867 | A1 | 3/2015 | Vronay et al. |
| 2018/0114000 | A1 | 4/2018 | Taylor |
| 2020/0081615 | A1 | 3/2020 | Lu et al. |
| 2021/0273812 | A1 | 9/2021 | Hardin et al. |
| 2023/0170079 | A1* | 6/2023 | Gnanasambandam ..................... G16H 50/70 705/2 |
| 2024/0038375 | A1* | 2/2024 | Mohtar .................. G16H 50/70 |
| 2025/0095860 | A1* | 3/2025 | Allen ..................... G16H 50/20 |
| 2025/0131998 | A1* | 4/2025 | Madhuripan .......... G16H 40/20 |
| 2025/0259041 | A1* | 8/2025 | Crabtree ................ G06N 3/047 |
| 2025/0272429 | A1* | 8/2025 | Roth ................... G06F 21/6245 |
| 2026/0031236 | A1* | 1/2026 | Neuberg ................ G16H 50/30 |
| 2026/0044490 | A1* | 2/2026 | Cunningham ...... G06F 16/2365 |
| 2026/0067335 | A1* | 3/2026 | Tran ................... G06F 21/6245 |

OTHER PUBLICATIONS

Hu et al., NIST SP 800-162, "Guide to ABAC," Jan. 2014 (rev. Aug. 2, 2019).

Birkholz, H., Thaler, D., Richardson, M., Smith, N., Pan, W., "Remote ATtestation procedureS (RATS) Architecture," IETF RFC 9334, Jan. 2023.

Lundblade, L., et al., "The Entity Attestation Token (EAT)," IETF RFC 9711, Apr. 2025.

Laurie, B., Messeri, E., Stradling, R., "Certificate Transparency Version 2.0," IETF RFC 9162, Dec. 2021.

HL7 International, "FHIR v5.0.0 (R5)—AuditEvent Resource," online specification page, accessed Jan. 7, 2026.

IHE International, "IHE IT Infrastructure Technical Framework—Audit Trail and Node Authentication (ATNA) Profile," accessed Jan. 7, 2026.

IHE International, "IHE IT Infrastructure Technical Framework Supplement: Add RESTful ATNA (Query and Feed)," Nov. 25, 2025.

Globalplatform, "Trusted User Interface API," Version 1.0, Public Release, Jun. 2013.

\* cited by examiner

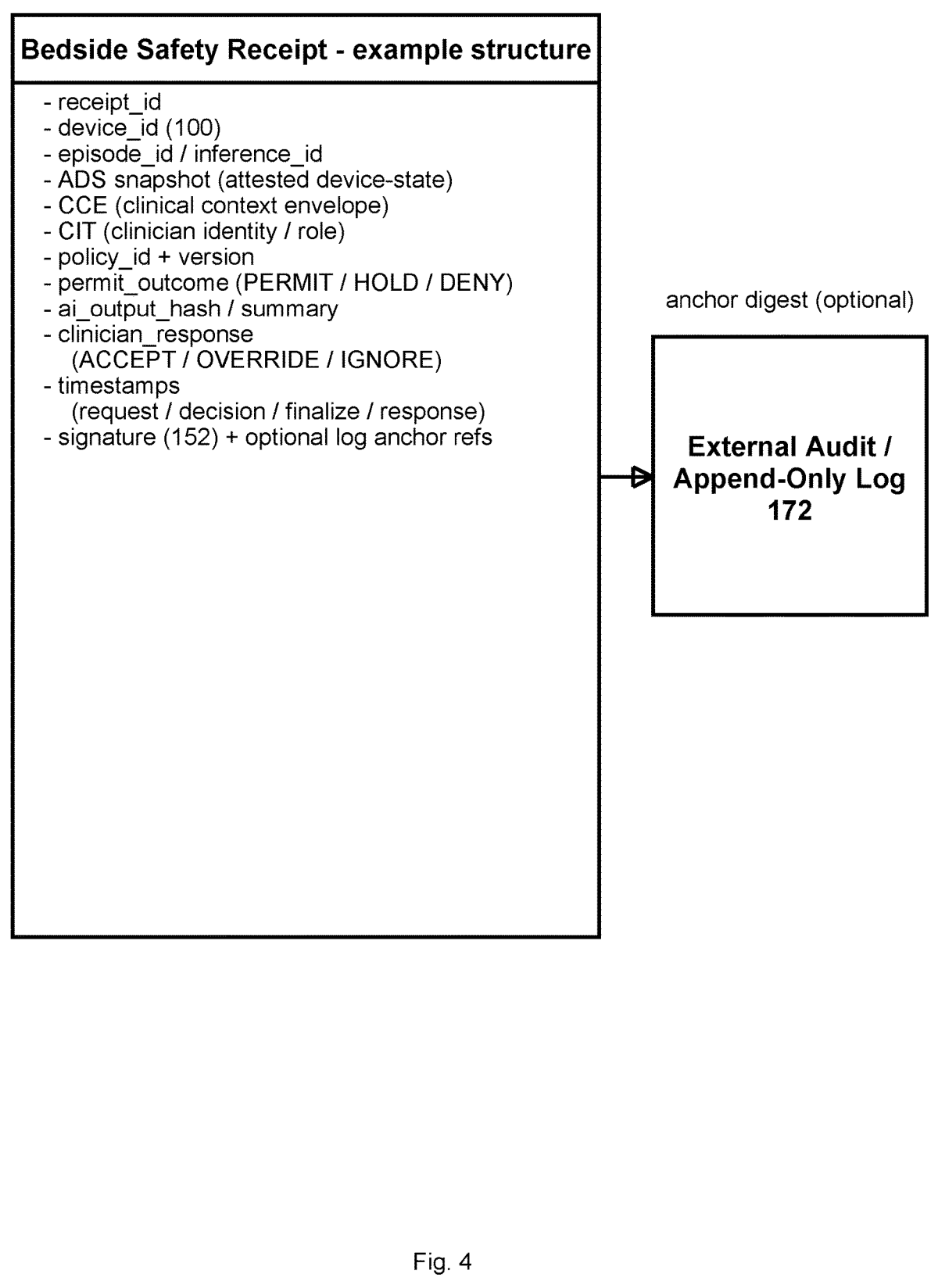

Bedside Safety Receipt - example structure

- receipt_id
- device_id (100)
- episode_id / inference_id
- ADS snapshot (attested device-state)
- CCE (clinical context envelope)
- CIT (clinician identity / role)
- policy_id + version
- permit_outcome (PERMIT / HOLD / DENY)
- ai_output_hash / summary
- clinician_response
    (ACCEPT / OVERRIDE / IGNORE)
- timestamps
    (request / decision / finalize / response)
- signature (152) + optional log anchor refs anchor digest (optional)

**External Audit /
Append-Only Log
172**

Fig. 4

BEDSIDE AI PERMIT-BEFORE-FINALIZATION GATE AND SAFETY RECEIPT RAIL FOR CLINICAL EDGE INFERENCE (Short description, non-limiting: Permit-before-finalization admission control at a bedside user-interface finalization gate corresponding to a user-visible commit boundary, using attested device-state, clinical context, and clinician identity; evaluating a policy graph to produce a permit outcome; fail-closed withholding of user-visible finalization absent a permit value; optionally inference-start attestation, time-bounded watchdog latching, short-lived anti-replay permit tokens, and/or require-override posture; with structured bedside safety receipts including policy/provenance identifiers and optional finalization provenance.)

II. CROSS-REFERENCE TO RELATED APPLICATIONS

Priority and incorporation (illustrative; non-limiting). This application claims priority to and the benefit of U.S. Provisional Patent Application No. 63/932,297, under 35 U.S.C. § 119(e), to the extent permitted. The disclosure of the provisional application is incorporated by reference for non-essential subject matter only, consistent with 37 C.F.R. § 1.57. In the event of any inconsistency between the provisional application and the present disclosure, the present disclosure controls; all essential material supporting the claims is provided explicitly herein.

Cross-rail context (illustrative; non-limiting). In some embodiments, the present disclosure can be used in conjunction with one or more co-pending applications by the same inventor(s) directed to:

trusted sensor ingress rails and Sensor Receipts for medical imaging (e.g., TSIL/TSIL-Scan)

safety receipt layers and permit-before-action gating for AI-assisted clinical decision support interventions (e.g., HTI)

safety risk budget engines and safety evidence receipts (e.g., SRBE)

revenue-cycle governance rails and revenue-cycle truth receipts (e.g., TRC/RCM)

AI-governed billing gate receipts and authorization-to-claim binding receipts (e.g., HTI2/A-Prime), including evidentiary bindings between safety receipts and billing or authorization receipts.

pharmacy prior authorization governance rails producing standardized pharmacy decision receipts and replay-verifiable auditability (e.g., PTR Rail), including evidentiary cross-rail references between bedside safety receipts and downstream authorization or audit receipts.

Evidence-only cross-rail notice (illustrative; non-limiting). Cross-rail references and bindings, including, by way of example and not limitation, evidentiary references to downstream authorization, billing, and/or pharmacy prior authorization governance rails producing standardized decision receipts and replay-verifiable auditability (e.g., PTR Rail), are evidentiary overlays that do not alter the BAPR permit-before-finalization nucleus; rails may be deployed independently; the claims control.

Incorporation by reference (non-essential only). Any referenced co-pending applications are incorporated by reference only for non-essential subject matter to the extent permitted by 37 C.F.R. § 1.57. All essential material supporting the claimed invention is provided explicitly in this specification. In the event of inconsistency, the present disclosure controls; the claims control.

No admission. Identification of any regulation, guideline, device class, network, protocol, or system is not an admission of prior art or common general knowledge.

III. FIELD

The present disclosure relates generally to the governance of AI systems in healthcare environments, and more particularly to bedside or point-of-care clinical devices that perform on-device AI inference. The disclosure describes a Bedside AI Permit & Safety Receipt Rail (BAPR) that gates AI inference and/or AI output finalization on such devices using attested device-state, clinical context, and clinician identity, and emits structured bedside safety receipts for audit, safety monitoring, model lifecycle governance, and downstream programmatic use. In some embodiments, governance is strengthened by inference-start attestations, time-bounded watchdog latching, and short-lived anti-replay permit tokens that gate user-interface finalization.

Patient-safety and trust objective (informative; non-limiting). In some embodiments, the disclosed permit-before-finalization control-path gating and structured bedside safety receipts provide technical safeguards configured to reduce preventable harm from unverified AI outputs in high-stakes bedside settings, support clinicians and care teams in delivering safe care, and improve auditability and accountability that support trust for patients, families, and other affected parties, including in resource-constrained environments. This statement is informative and non-limiting and does not alter claim scope; the claims control.

Consent-latch as governance input (illustrative; non-limiting). In some embodiments, the clinical context envelope further encodes or references verifiable patient (or authorized agent) consent evidence and associated consent-latch time anchors used as policy inputs for permitting user-interface finalization and/or downstream write-back.

IV. BACKGROUND

Bedside and point-of-care devices such as portable ultrasound probes, bedside ECG monitors, multi-parameter patient monitors, anesthesia carts, mobile imaging carts, and, in some deployments, interventional or robotic consoles that present AI-assisted guidance increasingly embed AI models that perform on-device inference. These models may assist with triage, measurements, image interpretation, alerting, or procedural guidance.

Unlike server-based clinical decision support systems that typically integrate with electronic health record (EHR) systems and benefit from centralized governance controls, bedside AI functionality may be deployed as firmware and/or applications across fleets of individual devices. Such deployments can create "shadow A" paths in which AI outputs are rendered directly on device displays without:

verifiable binding to a specific patient, encounter, episode, and/or order relevant to the displayed output;

assurance that the device is operating in a safe power, temperature, calibration, and/or configuration state at the time of display;

assurance that a properly authenticated clinician (and, where applicable, an authorized role) is in control of the device session;

verifiable linkage to applicable patient (or authorized-agent) consent evidence and/or authorization for the episode/order, in a manner resistant to replay and post-hoc injection; or durable evidentiary records of what AI outputs were shown, when they were finalized at a user-interface commit boundary (e.g., a user-interface finalization gate), and how clinicians responded.

Existing security and attestation frameworks for medical devices focus on establishing device integrity and communication security, but do not provide clinical governance semantics such as permit-before-action gating of AI inference based on clinical context or safety receipts that capture the clinical circumstances and human response surrounding each AI inference episode.

In addition, bedside environments may impose bounded response needs. Without explicit time-bounded gating, systems may degrade into permissive behavior under verification pressure (e.g., showing AI output despite incomplete checks), or may permit stale cached policies or stale permits to be reused across episodes.

There is therefore a need for a bedside or point-of-care rail that:

operates at the device or device-adjacent OS/app layer;

enforces permit-before-action semantics over AI inference and UI finalization using attested device-state, clinical episode binding, and clinician identity;

can fail-closed deterministically, including under connectivity loss and under time pressure; and emits structured, tamper-evident bedside safety receipts that integrate with broader clinical AI safety and governance stacks.

V. SUMMARY

Overview. In one aspect, a Bedside AI Permit & Safety Receipt Rail (BAPR) is provided. BAPR executes on or adjacent to a bedside clinical device that hosts one or more AI inference engines. BAPR intercepts AI inference requests and/or user-interface rendering and/or finalization requests, collects governance inputs including a device-state vector, a clinical context envelope, and a clinician identity token, evaluates a policy graph to compute a permit outcome, and enforces permit-before-action semantics by gating AI output finalization at a user-interface finalization gate.

Permit outcome taxonomy (illustrative; non-limiting). In some embodiments, the permit outcome is selected from outcomes comprising PERMIT, PERMIT_WITH_GUARD-RAILS, REQUIRE_OVERRIDE, HOLD, and DENY, where REQUIRE_OVERRIDE denotes that an explicit override indicator or attestation is required prior to finalization under policy, and HOLD denotes a retriable deficit posture.

Consent-latch gating (illustrative; non-limiting). In some embodiments, the governance inputs further comprise consent evidence associated with a patient or an authorized agent, wherein the consent evidence is cryptographically bound to at least one of an episode identifier or an order/procedure identifier and is verified at a commit boundary, the commit boundary comprising at least one of the user-interface finalization gate or a downstream write-back boundary, such that absent a satisfied consent-latch condition the system fail-closes to HOLD or DENY and prevents finalization.

UI finalization gate (broad; non-limiting). A "user-interface finalization gate" includes any commit boundary at which output becomes user-visible or clinically actionable, including without limitation: a UI render commit hook, display composition layer, display driver commit hook, framebuffer commit boundary, overlay compositor, message bus to a display service, or a functionally equivalent user-visible commit point. Embodiments may implement one or multiple such gates.

Finalization surfaces (illustrative; non-limiting). In some embodiments, user-interface finalization includes committing an alert, notification, or other clinician-facing signal derived from the AI inference output via a user-visible channel, including a device UI alert region, a notification service, or an equivalent clinician-facing surface.

Attested inputs (illustrative; non-limiting). In some embodiments, the device-state vector includes battery state-of-charge, AC versus DC power status, device temperature, one or more firmware/software integrity attestation results, and one or more indicators of whether safety-critical self-checks or calibration checks are satisfied. The clinical context envelope can encode or reference one or more episode, encounter, order, and/or procedure-scope identifiers, a care location, and a hashed or pseudonymized patient identifier. The clinician identity token can represent an authenticated clinician identity and role derived from a badge tap, login, smart card, biometric authentication, or other credential mechanism.

Policy and provenance pinning (illustrative; non-limiting). In some embodiments, the governance inputs further comprise one or more provenance identifiers and time anchors used to bind a permit outcome to a specific governance configuration and applicability window, including, by way of example and not limitation: a policy identifier and at least one of a policy_version, policy_digest, or policy_epoch; and one or more time anchors, including in some embodiments a monotonic time source and/or a commit-time anchor. In some embodiments, the governance inputs further include one or more inference provenance identifiers, such as an ai_model_id and/or ai_model_version and/or a model_config_digest and/or an inference-start attestation reference, and such provenance identifiers may be recorded in the bedside safety receipt to support replay-verifiable auditability and lifecycle governance, without requiring any particular policy format, model format, or attestation technology.

Consent evidence as a governance input (illustrative; non-limiting). In some embodiments, the clinical context envelope (CCE) includes or references consent evidence associated with a patient or an authorized agent and associated with at least one of an episode identifier, encounter identifier, order identifier, or procedure scope, wherein the consent evidence is integrity-protected by at least one of a digital signature, an attestation, or a digest commitment.

Time-of-consent latch (TOCTOU defense; illustrative; non-limiting). In some embodiments, BAPR binds finalization eligibility to a time-of-consent latch comprising at least (i) a consent effective window and (ii) a consent cutover time anchor, such that post-hoc consent edits, stale consent reuse, revocation/withdrawal, or ambiguous applicability deterministically map to HOLD and/or DENY unless remediated by recorded remediation under policy, including, in some embodiments, a subsequent signed record and/or bedside safety receipt that references the applicable episode/order/procedure scope and encodes an updated consent applicability assertion and/or authorized override provenance.

Commit-time consent verification (illustrative; non-limiting). In some embodiments, the user-interface finalization gate verifies, at commit time, that applicable consent evidence is present, unexpired, and scope-consistent with the observed episode/order and at least one of a ui_commit- _scope identifier or a finalization_gate_id, and fail-closes by preventing finalization absent a valid consent-latch condition.

Consent-bound permit tokens (illustrative; non-limiting). In some embodiments, the short-lived permit token (SLPT) is further bound to a consent digest and/or consent receipt reference and to at least one of a ui_commit_scope identifier or a finalization_gate_id, such that a token valid for a different consent scope, episode, order/procedure scope, or UI commit scope cannot be replayed to authorize finalization.

Receipt emission. In another aspect, BAPR generates a bedside safety receipt for each governed inference episode. The receipt encodes at least the device identifier, a snapshot of the attested device-state vector, the clinical context envelope, clinician identity, policy identifiers, the permit outcome, a summary or digest of the AI output, and any captured clinician response (e.g., accept, override, ignore). The receipt can be digitally signed and optionally anchored to a tamper-evident audit structure and transmitted toward one or more external systems, such as an EHR, safety monitoring service, or model lifecycle management system.

Receipt codes (illustrative; non-limiting). In some embodiments, the structured bedside safety receipt encodes one or more deny/hold codes indicating at least one of: time-budget exceedance, token expiration, token replay detection, inference-start attestation failure, or consent-latch failures including consent missing, unverifiable, expired, revoked/withdrawn, scope mismatch, or replay detection, without requiring any particular code taxonomy.

Offline/degraded modes. In some embodiments, BAPR supports offline or degraded modes in which a cached policy graph is used within a defined freshness window. If the policy cache is stale or attestation cannot be completed, BAPR can fail-closed by denying or holding AI inference output finalization and presenting a safe-mode UI overlay while allowing non-AI device functions to continue where appropriate.

Time-bounded watchdog latch (optional; moat-builder). In some embodiments, BAPR enforces that permit evaluation completes within a configured decision time budget (T_ms). If required verification cannot complete within T_ms, BAPR fail-closes to HOLD or DENY and prevents AI output finalization. This prevents unsafe "late permit" behavior under load or partial failure.

Inference-start attestation (optional; moat-builder). In some embodiments, BAPR generates or obtains an Inference-Start Attestation (ISA) at inference start, committing to at least an episode identifier and an integrity indicator of code/configuration state (e.g., secure boot measurement and/or trusted execution environment report) and optionally a model identifier or model configuration digest. The ISA is used as an input to permit evaluation and recorded in the bedside safety receipt.

Short-lived anti-replay permit tokens (optional; moat-builder). In some embodiments, on PASS, BAPR issues a Short-Lived Permit Token (SLPT) comprising an expiration (TTL) and an anti-replay tuple (e.g., nonce/counter/epoch) and bound to at least the episode identifier and a ui_commit_scope identifier. The UI finalization gate verifies SLPT validity at commit time; absent a valid SLPT, BAPR prevents finalization and fail-closes.

Cross-rail references (evidence-only). In some embodiments, bedside safety receipts include cross-rail references to other governance receipts (e.g., sensor receipts, safety evidence receipts, revenue-cycle receipts). Such references are evidentiary overlays and do not alter the permit-before-action semantics enforced by BAPR; the claims control.

Conformance/badge-profile interoperation (evidence-only; illustrative; non-limiting). In some embodiments, a bedside safety receipt (or a digest and/or anchoring reference thereof) is consumed as a canonical evidence object under a declared conformance or badge profile by an external replay-verification validator that emits a signed conformance result (e.g., PASS/FAIL with deterministic reason codes) for purposes of conditioning downstream automation, audit, or compliance workflows. Such conformance results are evidentiary overlays and do not alter the permit-before-action semantics or fail-closed behavior enforced by BAPR; the claims control.

Single inventive concept (restriction-risk reducer; illustrative). All embodiments share a common control-path nucleus: AI inference output finalization at a bedside device is admitted only after policy evaluation over attested device-state, clinical context, and clinician identity, enforced at a user-interface finalization gate with fail-closed behavior. Optional enhancements (ISA, watchdog time budgets, SLPT tokens, anchoring, training filters, cross-rail references) are configurations of the same nucleus. Consent-latch inputs, when present, are evaluated as part of the same permit computation over governance inputs prior to commit-time finalization.

Technical effect/eligibility (illustrative; non-limiting). The disclosed BAPR improves the functioning of bedside clinical devices and associated computer systems by relocating policy verification into the user-interface finalization control path and enforcing a fail-closed admission invariant such that no user-visible finalization occurs prior to PASS. In time-bounded embodiments, the watchdog latch enforces bounded-latency admission under verification pressure, preventing unsafe "late-permit" states. In tokenized embodiments, commit-time token verification prevents replay and cross-episode reuse. These are machine-enforced operations at a commit boundary that cannot be performed as mental steps and that prevent inconsistent states in which unverified AI outputs become user-visible or clinically actionable.

VI. BRIEF DESCRIPTION OF THE DRAWINGS

FIG. 4 is a schematic view of an example bedside safety receipt structure.

VII. DETAILED DESCRIPTION OF EXAMPLE EMBODIMENTS

A. Conventions, Claim Control, and Invariants

Figure 1:
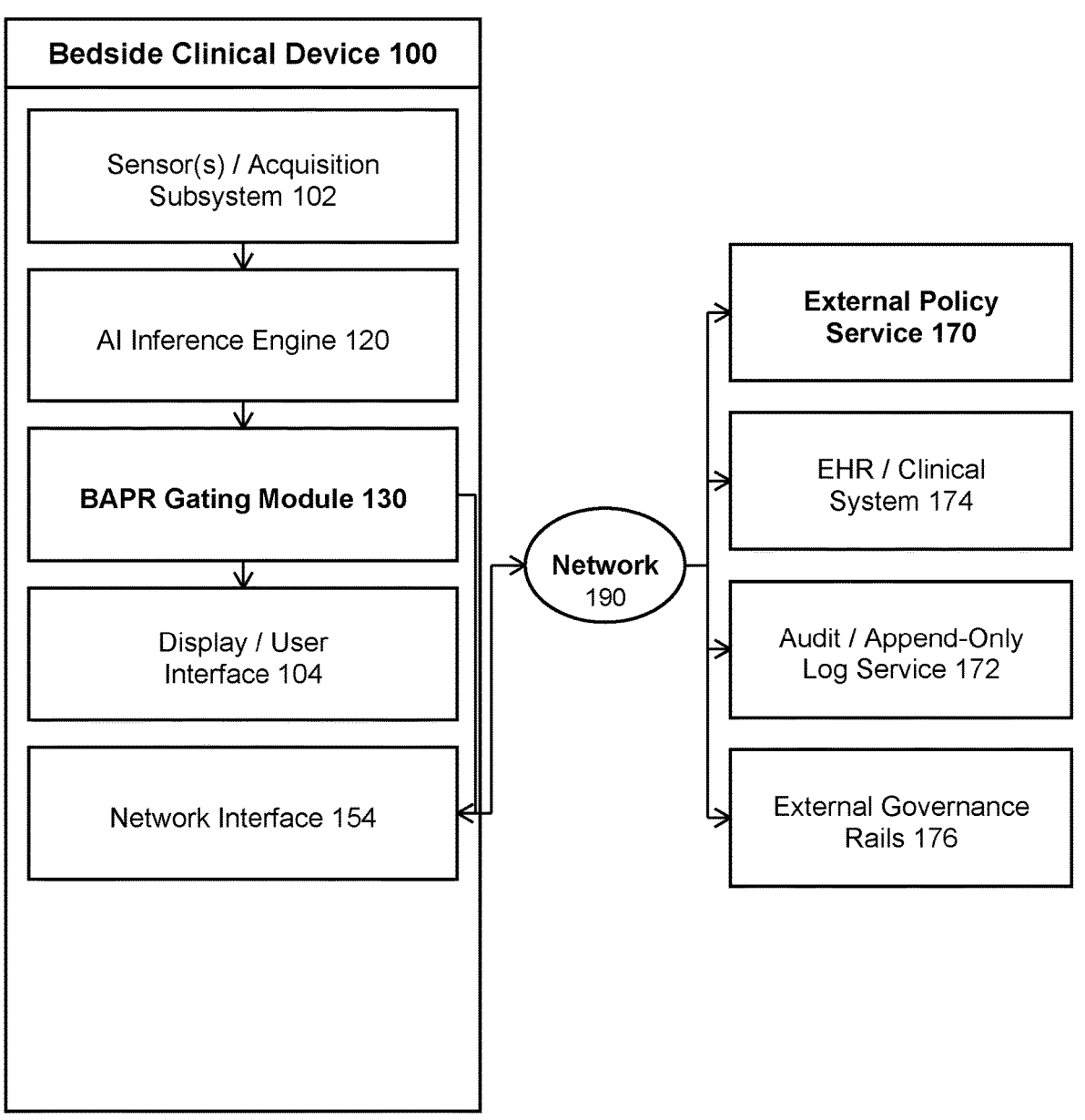
FIG. 1 is a block diagram of an example clinical environment including a bedside clinical device and external systems governed by BAPR.

Terms "MAY/SHOULD/MUST" are used in an illustrative sense and do not limit claim scope. Examples and profiles are illustrative; the claims control. No element invokes 35 U.S.C. § 112(f) absent "means for" or "step for."

PASS meaning (informative; non-limiting). "PASS" as used herein denotes that the computed permit outcome corresponds to a permit value (e.g., PERMIT or PERMIT_WITH_GUARDRAILS) under the active policy evaluation.

Order-of-operations invariant (illustrative; non-limiting). In some embodiments, the system enforces that policy evaluation and permit outcome computation complete prior to any AI output being finalized to a user-interface.

Idempotent finalization (illustrative; non-limiting). In some embodiments, the system applies an idempotency mechanism configured to ensure atomic finalization across retries at the user-interface finalization gate and any optional write-back boundary, the idempotency mechanism comprising at least one of an idempotency token, a transaction fence, a compare-and-swap-based commit marker, a write-ahead-log barrier, or a functionally equivalent control mechanism that prevents duplicate or split-brain finalizations across retries.

TOCTOU invariant (informative; non-limiting). Let permit_state $\in$ {INIT, HOLD, PASS, DENY} and ui_finalized be a boolean. Invariant: ui_finalized $\Rightarrow$ permit_state=PASS. Any observed UI finalization prior to PASS maps to DENY (illustrative) and may be recorded as an incident.

Time-budget invariant (illustrative; non-limiting). In embodiments using a watchdog latch, if (now —start_ time) >T_ms, then permit_state $\in$ {HOLD, DENY} and ui finalized=false.

Token invariant (illustrative; non-limiting). In embodiments using SLPT, ui_finalized $\in$(permit_state=PASS A SLPT_valid_at_commit=true).

Consent-latch invariant (illustrative; non-limiting). In embodiments in which consent-latch gating is enabled by policy, ui_finalized$\in$consent_latch_satisfied=true at commit time.

Evidence-only overlays do not narrow. Any schemas, deny-code taxonomies, profiles, test vectors, and example payloads are evidence-only overlays unless recited by claims.

B. REFERENCE NUMERALS

The following reference numerals may be used in the figures:
- 100—Bedside clinical device
- 102—Sensor(s) or acquisition subsystem (e.g., ultrasound probe, ECG leads)
- 104—Display or user-interface
- 106—User input interface (e.g., touchscreen, buttons, badge reader)
- 110—One or more processors
- 112—Memory storing instructions and data
- 120—AI inference engine
- 130—BAPR gating module (Bedside AI Permit Rail core)
- 132—Context collector module
- 134—Device-state attestor module
- 136—Clinician identity module
- 138—Policy evaluator/policy graph evaluator
- 140—UI enforcement/safe-mode overlay module
- 142—UI finalization gate (commit boundary)
- 150—Bedside safety receipt generator
- 152—Signing and anchoring module
- 154—Network interface
- 160—Local cache (policy cache, receipt buffer)
- 170—External policy service or configuration service

- 172—External audit or append-only log service
- 174—EHR or clinical system
- 176—External governance rails (e.g., TSIL-Scan, HTI, SRBE, TRC)

(Addendum Modules; Optional)
- 510—Inference-Start Attestation Generator (ISA-G)
- 500—Watchdog Latch Controller (WLC)
- 530—Short-Lived Permit Token Issuer (SLPT-I)
- 542—Permit Token Verifier (PTV)
- 570—Monotonic clock/timer source
- 580—Anti-replay tracker (nonce/counter registry)
- 590—Consent Evidence Collector (CEC)
- 592—Consent-Latch Verifier (CLV)
- 594—Consent revocation/rescission registry (CVR) (optional)

C. Example System Architecture (FIG. 1, FIG. 2)

Referring to FIG. 1, an example clinical environment includes a bedside clinical device 100 positioned near a patient in a care setting such as an emergency department, intensive care unit, operating room, labor and delivery suite, general ward, clinic, or home care setting. The bedside device 100 may be a portable ultrasound system, an ECG cart, a multi-parameter monitor, an anesthesia cart, an interventional console, or another point-of-care device.

The bedside device 100 includes one or more processors 110 and memory 112 storing instructions that, when executed, cause the bedside device 100 to implement at least an AI inference engine 120 and a BAPR gating module 130. The display 104 and user input interface 106 provide a human-facing user-interface for a clinician operating the device.

Figure 2:
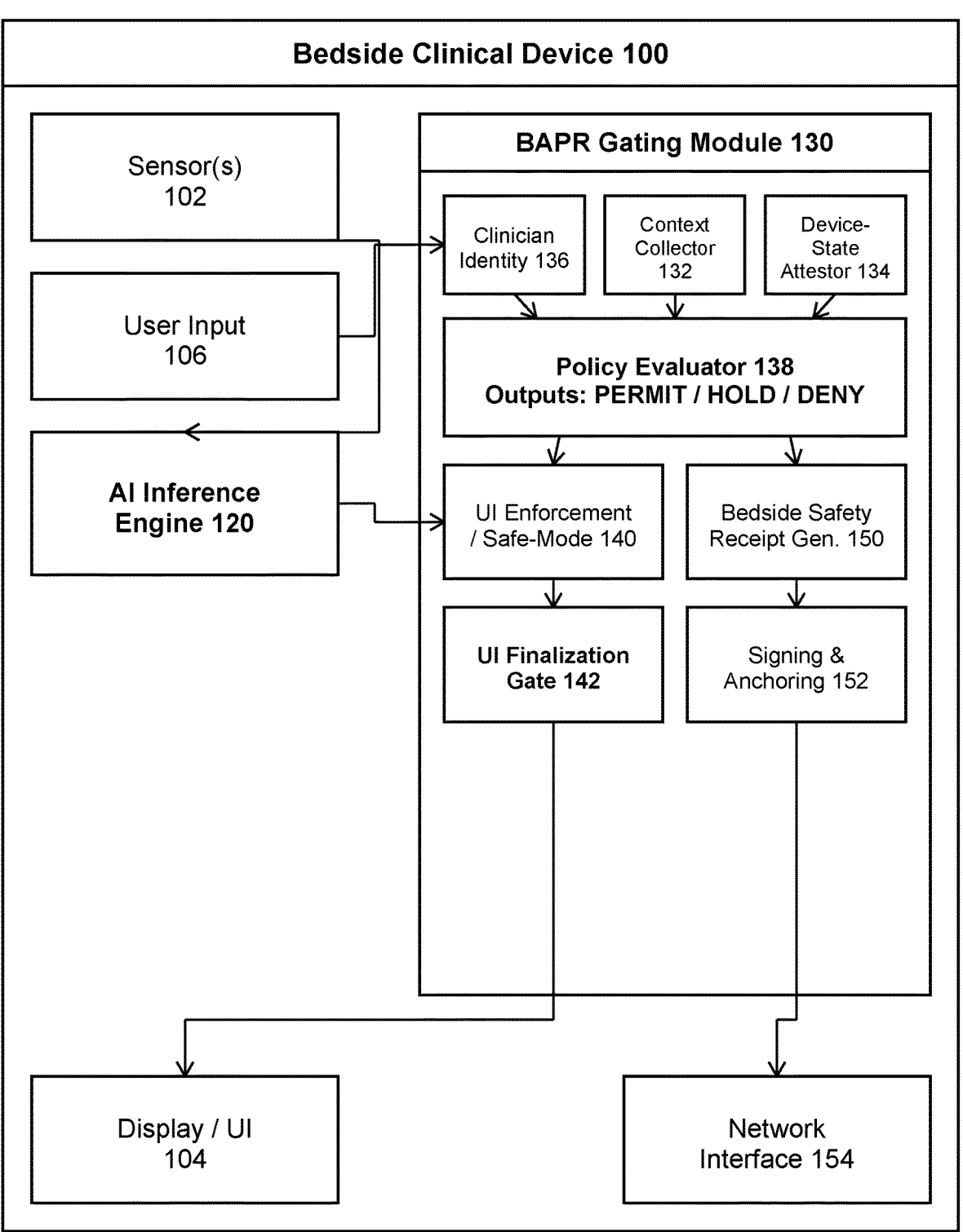
FIG. 2 is a block diagram of example internal components of a bedside device implementing BAPR, including a device-state attestor, context collector, policy evaluator, UI finalization gate, and bedside safety receipt generator.

As depicted in FIG. 2, the BAPR gating module 130 may include a context collector 132, a device-state attestor 134, a clinician identity module 136, a policy evaluator 138, a UI enforcement module 140, a UI finalization gate 142, and a bedside safety receipt generator 150 with a signing and anchoring module 152. These components may be implemented as software modules executing on processors 110, as firmware blocks, as OS services, as hypervisor hooks, or as combinations thereof.

The bedside device 100 may communicate via a network interface 154 with external systems, including an EHR 174, an external policy service 170, an external audit or append-only log service 172, and one or more external governance rails 176.

Placement in the critical path (non-limiting). The UI finalization gate 142 is placed in the critical path of user-visible AI output commitment. In some embodiments, any rendering call, message, DMA transfer, shared-memory update, or composition event that would make AI output user-visible MAY be intercepted and/or conditioned on PASS admission.

D. Bedside AI Inference Gating Flow (FIG. 3)

Figure 3:
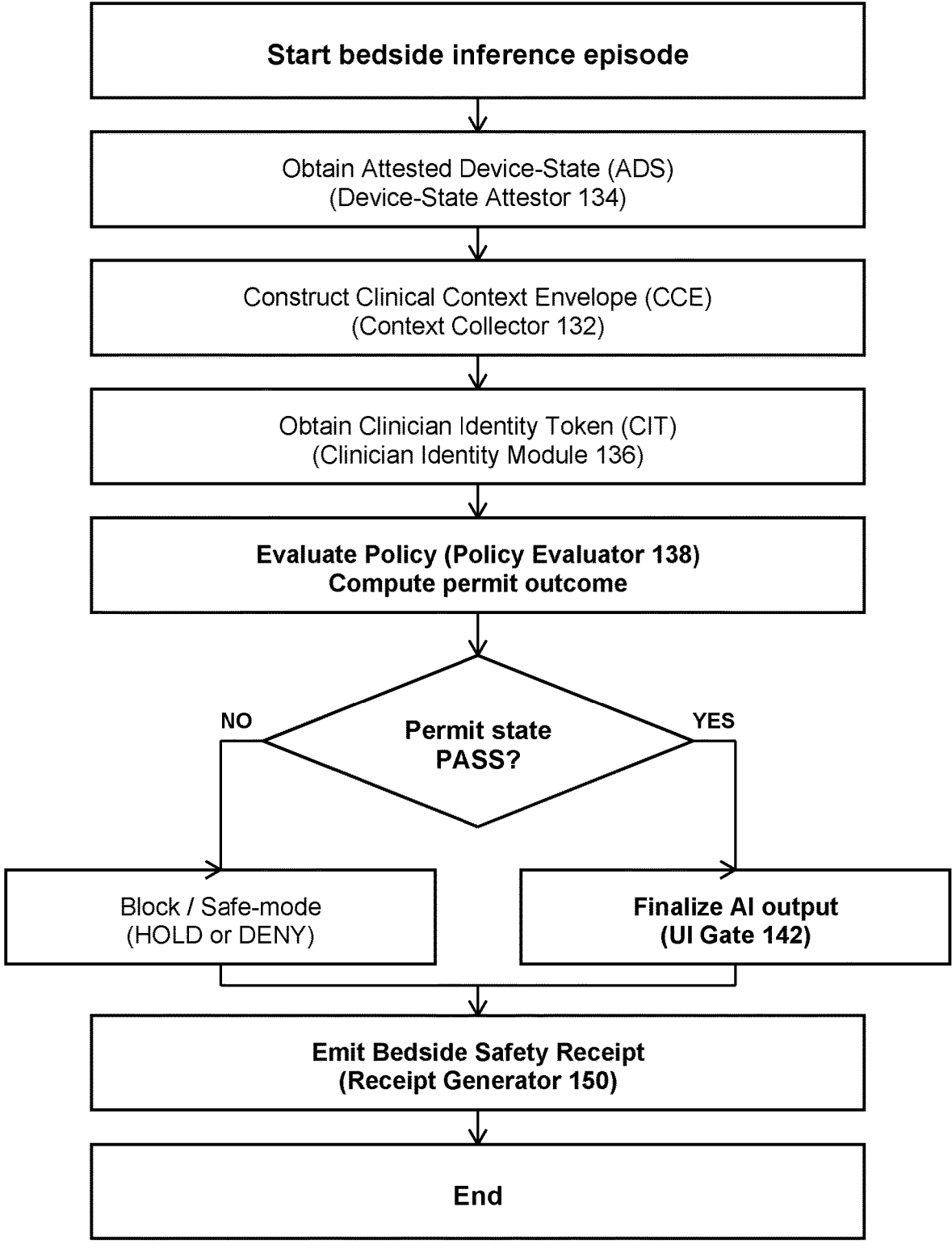
FIG. 3 is a flow diagram illustrating an example method of gating bedside AI inference output finalization based on attested device-state, clinical context, and clinician identity, and emitting a bedside safety receipt.
Figure 5:
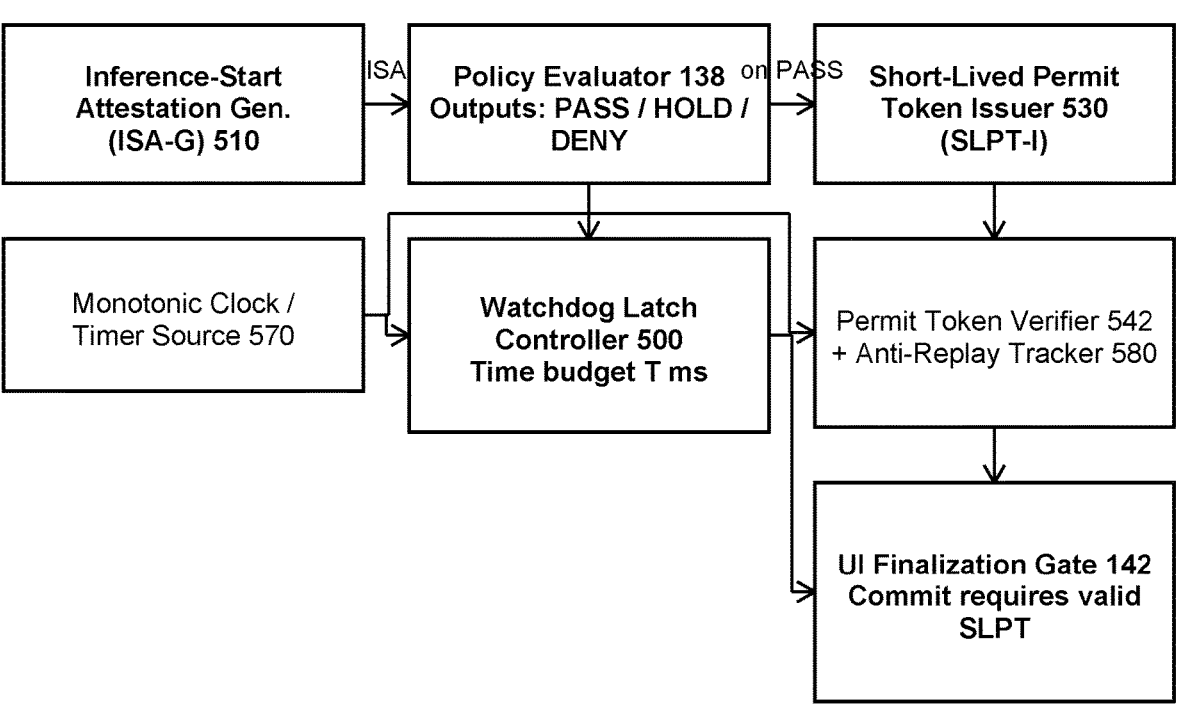
FIG. 5 is a schematic view of an optional time-bounded watchdog permit latch bound to an inference-start attestation and issuing a short-lived anti-replay permit token verified at a UI finalization gate.

Referring to FIG. 3, when a clinician initiates an AI-assisted operation on the bedside device 100, the AI inference engine 120 generates an inference request referencing a bedside inference episode. The inference request is intercepted by the BAPR gating module 130.

The device-state attestor 134 obtains or computes an attested device-state vector (ADS), which may include: battery state-of-charge and thresholds; power source (AC/DC); device or sensor temperature; firmware/software integrity attestation results; self-test/calibration status; and degraded/unsafe mode indicators.

The context collector 132 constructs a clinical context envelope (CCE) for the inference episode. In some embodiments, CCE encodes or references: a clinical episode/encounter/order identifier; a pseudonymized/hashed patient identifier; care setting/location; modality/acquisition parameters; and timestamps or sequencing information.

The clinician identity module 136 obtains a clinician identity token (CIT) for the clinician operating or supervising the bedside device 100, derived from login sessions, smart card/badge taps, biometric authentication, or equivalent credential mechanisms. CIT may include role or privilege information relevant to policy evaluation.

Role/privilege examples (illustrative; non-limiting). In some embodiments, role or privilege attributes encoded by a clinician identity token include, by way of example and not limitation, attending physician, supervising physician, resident physician, fellow, advanced practice provider, nurse, technician, or functionally equivalent role designations.

Consent evidence collection (illustrative; non-limiting). In some embodiments, the context collector 132 and/or an optional consent evidence collector 590 obtains consent evidence from at least one consent channel comprising a patient-facing UI, a witness workflow, an authorized-agent workflow, or a remote e-consent service, and produces a consent reference and/or consent digest bound to the episode/order identifiers in the CCE for policy evaluation.

Consent-latch verification (illustrative; non-limiting). In some embodiments, the consent-latch verifier 592 evaluates a consent-latch condition by verifying, at least: (i) integrity protection of the consent evidence and a cryptographic binding between the consent evidence and at least one identifier in the clinical context envelope (e.g., episode_id, order_id, and/or procedure-scope identifier); (ii) applicability at commit time using a consent effective window and a consent cutover time anchor; (iii) revocation/withdrawal status, including in some embodiments by consulting a consent revocation/rescission registry 594; and (iv) scope consistency with at least one of a ui_commit_scope identifier or a finalization_gate_id. In some embodiments, the system further detects replay or reuse of a consent binding across episodes/scopes using an anti-replay tracker 580 or an equivalent mechanism and fails closed in response. In some embodiments, failures are classified using one or more consent-related hold/deny codes and recorded in the bedside safety receipt.

The policy evaluator 138 evaluates a policy graph or ruleset that takes as input at least ADS, CCE, and CIT to produce a permit outcome selected from enumerated outcomes such as PERMIT, PERMIT_WITH_GUARDRAILS, REQUIRE_OVERRIDE, HOLD, or DENY Integrity hard veto (illustrative; non-limiting). In some embodiments, the policy graph includes an integrity predicate such that when an integrity indicator in the inference-start attestation is outside an allowed set of values under policy, the permit outcome is forced to a non-permit outcome regardless of other governance inputs.

The UI enforcement module 140 and UI finalization gate 142 enforce permit-before-action semantics by controlling whether and how the AI inference engine 120 can finalize outputs to the user-interface. For example, if permit outcome is DENY or HOLD, the system may suppress AI output, replace an AI output region with a safe-mode overlay, require escalation, or require an explicit override by an authorized clinician. In some embodiments, when the permit outcome is REQUIRE_OVERRIDE, the system withholds finalization unless a corresponding override indicator or attestation satisfying policy is obtained.

Optional write-back/actuation finalization (illustrative; non-limiting). In some embodiments, the same permit-before-action semantics enforced at the user-interface finalization gate are additionally applied to device-initiated write-back or actuation side effects, including transmitting measurements, annotations, or documentation artifacts to an EHR or external system, such that such side effects are denied absent PASS or an authorized override under policy. In some embodiments, such write-back boundaries include order/procedure submission commits, and commit-time admission may additionally require a valid consent-latch condition under policy.

Commit-time consent enforcement across boundaries (illustrative; non-limiting). In some embodiments, upon a user-interface finalization attempt and/or a write-back attempt, the system performs commit-time enforcement by re-checking the consent-latch condition at the applicable commit boundary, including at least one of the user-interface finalization gate 142 or a write-back boundary verifier, and prevents commit unless the consent-latch condition is satisfied (or an authorized override under policy is recorded). In some embodiments, the commit-time enforcement records, in the bedside safety receipt, at least one of: a consent_latch_satisfied indicator, a consent_ref/consent_digest, a consent_time_anchor, and a commit boundary identifier.

If permit outcome is PERMIT or PERMIT_WITH_GUARDRAILS, the system may allow rendering subject to guardrails, including suppressing a type of predicted value/risk score, adding warnings, limiting an output region, requiring dual-ack, or requiring supervised confirmation.

Co-sign/supervisory confirmation (illustrative; non-limiting). In some embodiments, the policy graph applies a co-sign or supervisory confirmation requirement such that finalization is denied unless an additional clinician identity token corresponding to a supervisory role is obtained and at least one acknowledgment associated with the supervisory role is observed and recorded.

Risk- or acuity-conditioned supervision (illustrative; non-limiting). In some embodiments, the policy graph classifies a subset of bedside inference episodes as higher-risk or higher-acuity based on clinical context and, for such subset, requires the supervisory clinician identity token and corresponding acknowledgment prior to treating an outcome as a permit value for user-interface finalization.

E. UI Finalization Gate (Broad Equivalents; Design-Around Hardener)

Commit boundary equivalence (illustrative; non-limiting). The UI finalization gate 142 may be implemented as:
  (a) a UI composition service hook;
  (b) a display driver submit hook;
  (c) a framebuffer commit hook;
  (d) a DMA fence/descriptor validation layer;
  (e) a secure overlay manager;
  (f) a privileged IPC gateway to the UI server; or
  (g) a functionally equivalent boundary that prevents AI output from becoming user-visible absent PASS.

No single implementation required. The disclosed gating semantics do not require any particular graphics stack, symbol encoding, dictionary, or visibility mask mechanism. The gate may operate on arbitrary AI output payloads, UI messages, overlays, regions, frames, textures, tiles, or equivalent content representations.

Rendering-constraint techniques (informative; non-limiting). For clarity, certain approaches may constrain display-time content by mapping AI tokens to constrained symbol/glyph dictionaries prior to pixel emission (including via a graphics-pipeline-resident state machine and/or visibility masking). When used solely as a rendering constraint and without enforcing permit-before-finalization admission control at a user-interface finalization gate corresponding to a user-visible commit boundary, such approaches do not, by themselves, provide the commit-boundary permit gating described herein and do not substitute for fail-closed admission control absent PASS. Such rendering-constraint techniques may optionally be used as supplementary guardrails in some embodiments; the claims control.

F. Bedside Safety Receipt Generation (FIG. 4)

For each governed inference episode, the bedside safety receipt generator 150 constructs a bedside safety receipt encoding a structured record of the episode. As illustrated in FIG. 4, a bedside safety receipt may include, by way of example and not limitation: a device identifier; a device-state snapshot (ADS); a clinical context envelope (CCE); clinician identity and/or role (CIT); policy identifier(s) and/or version information; a computed permit outcome; an AI output summary and/or content hash; a clinician response indicator (ACCEPTED/OVERRIDDEN/IGNORED/OTHER); and one or more timestamps for request intercept, permit evaluation, user-interface rendering/finalization, and clinician response capture.

In some embodiments, the bedside safety receipt further includes finalization provenance fields, such as a finalization_gate_id and/or a ui_commit_scope identifier corresponding to a commit boundary instance and/or authorized finalization surface, without requiring any particular UI stack or rendering pipeline. In some embodiments, the bedside safety receipt further includes consent reference fields, such as a consent_ref and/or consent_digest and a consent_time_anchor, associated with applicable patient (or authorized-agent) consent evidence.

Clinician response capture (illustrative; non-limiting). In some embodiments, clinician response indicators are recorded in the bedside safety receipt whether or not finalization was allowed, including in denied or degraded episodes.

Identity, acknowledgment, override, and consent provenance in receipts (illustrative; non-limiting). In some embodiments, the bedside safety receipt encodes: (i) an identity snapshot for one or more clinician identity tokens; (ii) one or more acknowledgment fields indicating whether supervisory confirmation and/or dual-ack was required and observed; (iii) override provenance comprising at least a reference to an override action and a reference to the clinician identity token used for the override; and (iv) consent provenance comprising at least a reference to a consent event and an applicability scope indicator.

The signing and anchoring module 152 can digitally sign the bedside safety receipt and optionally anchor a commitment or hash of the receipt to a tamper-evident audit structure. In some embodiments, the tamper-evident audit structure supports integrity commitments and verifiable inclusion and/or continuity properties (e.g., signed heads and/or authenticated proofs), without requiring any particular log format or proof system.

Evidence-only anchoring (illustrative; non-limiting). Anchoring is an evidentiary overlay that strengthens auditability but is not required for the core permit-before-action gating semantics unless a claim expressly recites anchoring.

The bedside device 100 may transmit bedside safety receipts via the network interface 154 toward an EHR 174, external governance rails 176, safety monitoring services, or model lifecycle management pipelines. Receipts may include cross-rail references to other receipts (sensor receipts, safety evidence receipts, revenue-cycle receipts) for the same episode.

G. Optional: Inference-Start Attestation (ISA)

In some embodiments, an inference-start attestation generator (ISA-G) 510 generates or obtains an Inference-Start Attestation (ISA) at or near inference start, before any AI output is eligible for UI finalization.

ISA contents (illustrative; non-limiting). ISA may commit to one or more of: episode_id; encounter/order binding; model_id/version and/or model_config_digest; device/software integrity measurement digest; TEE attestation report; a monotonic counter; a timestamp; and a signature or MAC under a device key.

Start-binding. In some embodiments, policy evaluation consumes ISA as an input, and bedside safety receipts store an isa_id or isa_digest, enabling later verification that permit decisions corresponded to a trustworthy inference start.

H. Optional: Time-Bounded Watchdog Permit Latch

In some embodiments, a watchdog latch controller (WLC) 500 enforces a configured decision time budget T_ms for permit evaluation. T_ms may be workflow-dependent (e.g., triage, monitoring, infusion, interventional guidance).

Time budget calibration (illustrative; non-limiting). In some embodiments, the decision time budget T_ms is configured based on at least one of: (i) a clinical workflow category, (ii) a risk level or harm budget associated with the AI inference output and/or the bedside inference episode, and (iii) a device capability profile of the bedside clinical device, without requiring any particular risk scoring framework.

Fail-closed under verification pressure. If policy evaluation, ISA verification, or required attestation validation cannot complete within T_ms, the system forces HOLD or DENY and prevents UI finalization of AI outputs, optionally rendering a safe-mode overlay.

Backpressure and retry. In some embodiments, HOLD includes retry_after_ms and idempotency_key to suppress duplicate attempts and enforce backoff.

I. Optional: Short-Lived Anti-Replay Permit Tokens (SLPT)

In some embodiments, upon a permit outcome corresponding to PERMIT or PERMIT_WITH_GUARDRAILS, a short-lived permit token issuer (SLPT-I) 530 issues an SLPT comprising: (i) expiration/TTL, (ii) an anti-replay tuple (nonce/counter/epoch), and (iii) bindings to at least episode_id and a ui_commit_scope identifier.

Anti-replay monotonicity (illustrative; non-limiting). In some embodiments, the anti-replay tuple includes a monotonic counter maintained per episode_id and/or per ui_commit_scope, and the system enforces a monotonicity constraint such that tokens presenting non-monotonic counter values for a given episode_id or ui_commit_scope are treated as replayed and denied.

A permit token verifier (PTV) 542 at the UI finalization gate 142 verifies SLPT validity at commit time, including expiration and anti-replay checks (using an anti-replay tracker 580), and denies UI finalization absent a valid SLPT.

Token digest in receipts (privacy-preserving). In some embodiments, bedside safety receipts store slpt_id or slpt_digest rather than raw token contents.

Non-reuse. In some embodiments, SLPT is single-use or bounded-use per episode and commit scope; reuse attempts yield TOKEN_REPLAY or ANTI_REPLAY_FAIL and map to HOLD/DENY

J. Offline and Degraded Modes

The BAPR gating module 130 can maintain a local cache 160 of policy configurations obtained from the external policy service 170 with a policy freshness window. When connectivity is unavailable but cached policy is within the freshness window, permit outcomes may be computed using the cached policy.

If the policy cache is stale, if required attestations cannot be performed, or if required verification cannot complete within a time budget (when configured), BAPR transitions to a degraded mode and forces permit outcomes to HOLD or DENY, presenting a safe-mode overlay while allowing non-AI functions to continue where appropriate.

Bedside safety receipts can record degraded policy state and can be buffered locally until connectivity is restored.

K. Training, Monitoring, and Programmatic Uses (Evidence-Only Overlays)

Downstream systems can use bedside safety receipts as governance evidence. Training pipelines may filter candidate training examples to include only bedside inference episodes whose receipts indicate valid device-state attestation, valid clinical context binding, and permit outcomes satisfying policy constraints.

Safety monitoring systems may aggregate bedside safety receipts to detect patterns of unsafe overrides, repeated inference under degraded device-state, or disparities in AI usage across populations or care settings.

Aggregated bedside safety receipts may be grouped into evidence bundles for submission to outcomes-based programs; such use is evidentiary only and does not alter the permit-before-action semantics enforced by BAPR.

Model update admissibility (illustrative; non-limiting; evidence-only). In some embodiments, a model lifecycle management pipeline consumes structured bedside safety receipts and/or evidence bundles to evaluate whether a candidate model configuration (e.g., ai_model_id, ai_model_version, and/or model_config_digest) is admissible for rollout under an update policy, and to determine an update disposition selected from outcomes comprising at least a permit value and a non-permit value. The update policy may evaluate aggregates and/or predicates derived from the receipts, including at least one of: (i) proportions of episodes whose receipts indicate valid device-state attestation and clinical context binding, (ii) distributions of permit outcomes, (iii) override incidence, or (iv) degraded-state incidence.

Signed update certification record (illustrative; non-limiting). In some embodiments, the pipeline generates a digitally signed update certification record encoding the candidate model configuration identifier, policy identifiers and version/digest/epoch information, and one or more receipt references (e.g., receipt digests and/or SignedReceiptIndex references) used to support the admissibility determination.

Withdrawal/rescission (illustrative; non-limiting). In some embodiments, when an update certification assertion is withdrawn, the pipeline publishes a signed rescission record that references the withdrawn certification assertion, consistent with signed rescission patterns. Such certification and rescission records are evidentiary and non-limiting and do not alter the permit-before-action semantics enforced by BAPR.

L. Equivalents (Non-Limiting)

Policy evaluation may be implemented using policy graphs, deterministic rule engines, bytecode VMs, decision tables, or functionally equivalent evaluators producing PERMIT/HOLD/DENY semantics.

Attestation mechanisms include secure boot measurements, TPM measurements, TEE reports, signed firmware manifests, sensor calibration attestations, or equivalents.

Token mechanisms include signed capability tokens, MAC'd decision records, ephemeral authorization headers, or equivalents providing the same anti-replay and TTL-bounded gating semantics.

UI finalization gates include any enforcement boundary preventing user-visible AI output absent PASS admission.

VIII. APPENDICES (OPTIONAL; ILLUSTRATIVE; EVIDENCE-ONLY)

Non-limiting/evidence-only notice. Appendices provide enablement aids, interoperability examples, audit tooling, and illustrative taxonomies. Unless a claim expressly recites an appendix element, appendix content is illustrative and does not alter claim scope; the claims control.

Order of precedence (illustrative). If any inconsistency is perceived, the claims control, then the Detailed Description, then the Figures, then the Appendices.

Appendices (illustrative; non-limiting; evidence-only examples). Appendices A-F form part of this Specification and provide, by way of example and not limitation: glossary entries; example data structures and canonical encodings for bedside safety receipts (including finalization provenance fields such as finalization_gate_id and/or ui_commit_scope, and, when applicable, consent_ref/consent_digest and consent_time_anchor); example structures for inference-start attestations (ISA) and short-lived permit tokens (SLPT); example deny/hold code groupings (including consent-latch failure codes); example conformance artifacts, test vectors, procurement/evaluation checklists, and transport-neutral interface stubs; and example threat models and mitigations for TOCTOU, replay, and degraded/offline operation. These materials aid enablement and implementation and are illustrative and non-limiting; nothing in the appendices is intended to limit claim scope, and the claims control.

Appendix A—Glossary (Selected; Non-Limiting)

Evidence-only/non-limiting notice. This glossary is provided to improve clarity and enablement. Unless a claim expressly recites a glossary element as a limitation, glossary content is illustrative and does not narrow claim scope; the claims control.

Functional equivalence. Each term includes functionally equivalent mechanisms that achieve the same admission/denial semantics, without requiring any particular vendor, protocol, wire format, UI stack, graphics pipeline, or attestation technology.

Non-trademark notice. "BAPR," "Bedside AI Permit & Safety Receipt Rail," and other labels are technical shorthand for convenience; no trademark rights are asserted herein.

A. Core Actors/Objects

AI inference engine. Software, firmware, hardware, or a combination thereof configured to execute one or more AI models to produce an AI inference output for a bedside inference episode.

AI inference output. Any output produced by an AI inference engine, including without limitation an interpretation, measurement, label, alert, recommendation, overlay, score, confidence metric, visualization, annotation, or other content intended to be rendered, displayed, transmitted, stored, or used to influence a clinical workflow or device behavior.

Bedside clinical device. A device located near a patient in a clinical or care setting and configured to acquire signals/images and to present information to a clinician, including without limitation portable ultrasound systems, ECG carts, multi-parameter monitors, anesthesia carts, imaging carts, interventional consoles, or robotic consoles operating under clinician supervision.

Bedside inference episode. A bounded transaction or period during which a bedside clinical device invokes an AI inference engine to generate an AI inference output related to one or more patient observations, acquisitions, measurements, or clinician-initiated tasks. An episode may be identified by an episode identifier and may be linked to encounter/order context.

BAPR (Bedside AI Permit & Safety Receipt Rail). A set of components executing on or adjacent to a bedside clinical device that intercepts inference requests and/or UI finalization events, evaluates policy over governance inputs, enforces permit-before-action semantics, and emits structured bedside safety receipts.

Evidence object. A structured artifact representing a governed event or outcome (e.g., a bedside safety receipt) that may be used for audit, monitoring, training governance, lifecycle governance, or downstream programmatic evaluation.

Structured bedside safety receipt. A structured, machine-readable record summarizing at least (i) governance inputs and context and (ii) the permit outcome for a bedside inference episode, and optionally (iii) output summaries/hashes and (iv) clinician response and timing fields. A receipt may be digitally signed and optionally anchored to a tamper-evident store.

B. Governance Inputs

Attested device-state vector (ADS). A structured set of one or more indicators describing the state of a bedside clinical device, where at least one indicator is derived from a cryptographic attestation or integrity mechanism (e.g., secure boot measurement, TEE report, signed firmware manifest) and at least one indicator corresponds to a safety-relevant operating limit or condition.

Permit outcome taxonomy harmonization (illustrative; non-limiting). In some embodiments, the permit outcome is classified as one of: PERMIT, PERMIT_WITH_GUARD-RAILS, REQUIRE_OVERRIDE, HOLD, or DENY, where REQUIRE_OVERRIDE denotes that explicit clinician attestation or override inputs are required prior to finalization, and HOLD denotes a retriable deficit posture under policy.

Device-state indicator. A scalar, categorical value, bit, or field describing device state, including without limitation power/energy state, temperature, firmware/software integrity, sensor calibration status, self-test status, degraded mode flags, or equivalent safety-relevant indicators.

Clinical context envelope (CCE). A structured set of identifiers/descriptors encoding context for a bedside inference episode, including at least one of an episode identifier, encounter identifier, or order identifier and a care location, and optionally a patient identifier (pseudonymized/hashed), modality, acquisition parameters, timestamps, or sequencing information.

Consent evidence. A verifiable record indicating patient or authorized-agent consent applicable to an episode/order/procedure scope, including functionally equivalent signed records, attestations, or digest commitments.

Consent effective window. A time interval or condition under which consent is applicable, including start/end anchors or equivalent applicability constraints.

Consent cutover time anchor. A time anchor used to evaluate consent applicability at commit time and to detect post-hoc edits or ambiguity.

Consent-latch condition. A policy-evaluable condition that is satisfied only when consent evidence is present, applicable, and valid at commit time for the relevant scope.

consent_ref/consent_digest. An identifier and/or digest that references or commits to consent evidence without requiring disclosure of raw consent contents.

Consent revocation/rescission record. A record indicating consent is revoked/withdrawn, including functionally equivalent revocation registries or signed rescission entries.

Care location. A location or unit within a care setting (e.g., ED, ICU, OR, ward, clinic, home care) and/or a device placement location identifier used to contextualize an episode for policy evaluation.

Clinician identity token (CIT). A token, identifier, or credential-derived representation indicating an authenticated clinician and optionally role/privilege attributes, derived from login, badge tap, smart card, biometric authentication, or functionally equivalent credential mechanisms.

Role/privilege attribute. A policy-relevant attribute associated with a clinician identity token (e.g., attending, resident, technician, supervising physician) used to determine permissions, guardrails, override eligibility, or required acknowledgments.

Pseudonymized or hashed patient identifier. A patient identifier transformed using hashing, tokenization, pseudonymization, or equivalent mechanisms to reduce direct identifier exposure while enabling deterministic linkage under policy.

C. Policy/Decisioning

Policy graph. A machine-evaluatable representation of rules, conditions, workflows, or constraints that map governance inputs (e.g., ADS/CCE/CIT and optional ISA) to a permit outcome, including without limitation decision tables, deterministic rule engines, policy graphs, bytecode policy VMs, or equivalent evaluators. In some embodiments, the SLPT is bound to at least the episode identifier and a ui_commit_scope identifier such that a token valid for one ui_commit_scope is non-transferable to a different scope at commit time.

Policy evaluator. A component configured to evaluate a policy graph or ruleset and compute a permit outcome based on governance inputs.

Policy identifier/policy version. An identifier, version identifier, digest, or epoch value indicating the policy configuration used to compute a permit outcome for an episode.

Policy freshness window. A time interval or condition within which a cached policy configuration is considered valid for use; outside the window, policy is treated as stale and may force degraded behavior.

Permit outcome. A value computed by policy evaluation indicating whether a governed action (e.g., UI finalization of AI output) is allowed and under what conditions. Illustrative outcomes include PERMIT, PERMIT_WITH_GUARD-RAILS, HOLD, and DENY Permit value. A permit outcome value indicating the action is allowed (e.g., PERMIT or PERMIT_WITH_GUARDRAILS), optionally subject to constraints.

Non-permit outcome. A permit outcome indicating the action is not allowed absent additional conditions, and comprising at least HOLD and/or DENY in some embodiments; non-permit outcomes prevent UI finalization unless an authorized override mechanism is satisfied under policy.

Guardrail. A constraint, modification, warning, suppression, or limitation applied when permitting an action, including without limitation suppressing certain outputs, requiring warnings, limiting display regions, requiring dual-ack, requiring supervised confirmation, or applying role-based constraints.

Override. A policy-governed clinician action that authorizes finalization or use of AI output despite a non-permit outcome or despite guardrail constraints, typically requiring elevated privilege, additional acknowledgments, or additional logging.

Dual-ack/supervised confirmation. A policy-governed requirement that two acknowledgments or a supervisory confirmation be obtained before finalization or clinical use of AI output proceeds.

D. Enforcement/Control Path

Permit-before-action configuration. A configuration in which evaluation of a policy graph and satisfaction of one or more permit conditions are enforced as preconditions to a governed action (e.g., UI finalization), such that the action cannot proceed unless the permit outcome corresponds to a permit value or an authorized override is recorded under policy.

User-interface finalization. A commit or completion event by which content becomes user-visible or clinically actionable, including without limitation final composition, driver submit, framebuffer commit, overlay commit, IPC-delivered UI commit, or functionally equivalent commit points.

User-interface finalization gate (UFG). A control boundary positioned in the critical path of user-interface finalization that prevents AI output from becoming user-visible or clinically actionable unless PASS admission is satisfied. A UFG includes without limitation a UI render commit hook, display composition layer, display driver commit hook, framebuffer commit boundary, overlay compositor, privileged UI service gateway, DMA fence/descriptor validation layer, or equivalents.

UI commit scope. A ui_commit_scope identifier describing what finalization is authorized for a permitted event, including without limitation a UI region, view identifier, session identifier, surface identifier, overlay identifier, frame identifier, commit boundary identifier, or equivalents.

Safe-mode overlay. A user-interface configuration or element rendered in place of or on top of an AI output region to indicate AI assistance is unavailable, constrained, degraded, or denied, while optionally allowing non-AI device functions to continue.

Non-AI device functions. Device capabilities not dependent on the gated AI output finalization, including acquisition, monitoring, display of raw sensor data, manual measurements, or other baseline device functions.

Fail-closed semantics. A behavior in which, upon failure to satisfy validation/attestation/policy/time-budget conditions, the governed action (e.g., UI finalization) is prevented rather than allowed, unless an authorized override is recorded under policy.

TOCTOU (time-of-check to time-of-use) race. A condition in which a check is performed but the relevant state changes before use; the disclosed gating semantics reduce TOCTOU by relocating enforcement into the UI finalization control path.

Critical path. The set of operations and boundaries that must be traversed for AI output to become user-visible or actionable; BAPR places enforcement into this path.

E. Addendum Moat Modules (ISA/Watchdog/Tokens)

Inference-Start Attestation (ISA). An attested event artifact generated or obtained at inference start that commits to at least an episode identifier and an integrity indicator of code/configuration state, and optionally model identifier/version, model configuration digest, counters, timestamps, and signatures/MACs.

Inference start event. The event at which an inference request begins execution or is admitted for execution; may be defined by firmware/OS hooks, TEE entry, inference engine start signal, or equivalents.

Integrity indicator. A cryptographically verifiable indicator describing code/configuration state, including without limitation secure boot measurements, TEE attestation fields, signed manifests, hash measurements, or equivalents.

Trusted execution environment (TEE). A hardware-backed or isolated execution environment capable of producing attestation evidence about code/configuration state and/or protecting sensitive computation.

Remote attestation report. A report or evidence object produced by a TEE or integrity mechanism that can be verified by a relying component to assess integrity indicators; reports may be local or remote in different embodiments.

Watchdog latch controller (WLC). A controller configured to enforce a configured decision time budget for permit evaluation and to force fail-closed outcomes when verification cannot complete within the budget.

Decision time budget ($T\_ms$). A configured maximum allowed time for completing permit evaluation and required verification steps; exceeding the budget maps to HOLD/DENY in time-bounded embodiments.

Decision latency. The measured elapsed time between a start marker (e.g., inference start or request intercept) and completion of permit evaluation and/or token issuance.

Monotonic clock. A clock or timer source that progresses monotonically (not subject to wall-clock adjustments) used for measuring time budgets, latencies, and expiration.

Short-Lived Permit Token (SLPT). A cryptographically verifiable token issued upon permit outcomes that includes an expiration (TTL or exp_ts), an anti-replay tuple, and bindings to at least episode identifier and UI commit scope; SLPT is verified at commit time by the UI finalization gate.

Expiration/TTL. A bounded validity interval for a permit token, expressed as an expiration timestamp, TTL duration, or functionally equivalent mechanism.

Anti-replay tuple. One or more fields (e.g., nonce, monotonic counter, epoch) used to prevent reuse or replay of a token outside its permitted context.

Nonce. A value intended to be unique (or highly unlikely to repeat) used as part of an anti-replay tuple.

Monotonic counter. A non-decreasing counter used to detect replay or reuse; may be per device, per session, per episode, or per scope.

Epoch. A versioned context value for token validity, policy context, or session context used to prevent cross-epoch reuse.

Permit token verifier (PTV). A verifier configured to validate SLPT authenticity, expiration, and anti-replay conditions at commit time.

Anti-replay tracker. A component maintaining state about used nonces/counters/epochs, enabling detection of token reuse or replay.

Token digest/token identifier. A digest or identifier representing a token without disclosing full token contents, used for privacy and audit logging.

F. Receipts/Audit/Tamper Evidence

Clinician response field. A receipt field capturing clinician action in response to AI output (e.g., ACCEPTED, OVERRIDDEN, IGNORED, OTHER), optionally with details, timestamps, or reasons.

Tamper-evident store. A storage mechanism that enables detection of modification or deletion of recorded entries, including without limitation append-only logs, authenticated data structures, WORM storage, signed journals, or equivalents.

Anchoring. Recording a commitment (e.g., hash/digest) of a receipt or event in a tamper-evident store such that later verification can detect alteration or omission.

Append-only log. A tamper-evident store that is append-only (entries are added without modifying prior entries) and may publish signed heads or equivalent integrity commitments.

Signed head. A signed commitment to a current state of an append-only log (e.g., tree head, set head, epoch head), enabling verifiers to assess freshness or continuity in embodiments that use such logs.

Inclusion proof Proof that a commitment corresponding to a receipt or digest is included in an authenticated structure, in embodiments that use authenticated data structures.

Consistency proof/append-only evolution. Proof that a later state of an append-only log extends an earlier state without altering prior entries, in embodiments that use such proofs.

Evidentiary overlay. A feature that strengthens auditability or interoperability (e.g., anchoring, cross-rail references, schema stubs) but does not alter the core permit-before-action semantics unless recited in claims.

G. Connectivity/Caching/Degraded Behavior

Local cache. On-device or device-adjacent storage used to retain policy configurations and/or buffered receipts during disruptions.

Degraded policy state. A state in which BAPR lacks a valid or fresh policy configuration or cannot complete required attestations/verifications, and in which permit outcomes are constrained (e.g., defaulting to HOLD/DENY) with safe-mode behaviors.

Connectivity disruption. Loss or degradation of network connectivity to external policy services, audit services, EHR systems, or governance rails.

Freshness window. A time interval within which cached data (policy, attestations, or supporting artifacts) is treated as sufficiently current under policy; outside the window, treated as stale.

Buffered receipts. Receipts stored locally during disruptions and transmitted upon restoration of connectivity.

H. External Systems/Cross-Rail Interoperability

External policy service. A service providing policy configurations, updates, versions, or rule parameters used by the policy evaluator; may be local, remote, centralized, distributed, or hybrid.

Electronic health record (EHR). A clinical information system that may receive receipts or derived summaries; inclusion is illustrative and not limiting.

Model lifecycle management pipeline. A set of systems for monitoring, updating, validating, and governing AI models, which may consume receipts as evidence of executed episodes and outcomes under policy.

Safety monitoring service. A service that aggregates receipts to detect trends such as unsafe overrides, repeated degraded modes, device-state violations, or usage disparities.

External governance rails. Other governance systems that may produce receipts or accept receipt references, including imaging sensor ingress rails, safety receipt layers, risk budget engines, or revenue cycle truth rails.

Cross-rail reference. A reference, pointer, or identifier in a bedside safety receipt that links to another receipt or governance artifact for the same episode; cross-rail references are evidentiary only unless recited by claims.

Evidence bundle. An aggregate view, package, or collection of receipts or derived metrics for a window, used for audit, monitoring, procurement, or programmatic evaluation; evidence bundles are evidentiary overlays.

I. Denials/Holds/Operational Codes (Non-Limiting)

Denial code/hold code. A machine-readable code indicating a predicate failure or retriable deficit; code taxonomies are evidence-only and do not narrow claim scope unless recited by claims.

TIME_BUDGET_EXCEEDED. A code indicating permit evaluation exceeded the configured decision time budget in watchdog embodiments; maps to fail-closed HOLD/DENY START_ATTEST_FAIL. A code indicating inference-start attestation is missing, invalid, unverifiable, or inconsistent with required integrity predicates.

TOKEN_REQUIRED. A code indicating UI finalization attempted without a required permit token in tokenized embodiments.

TOKEN_EXPIRED. A code indicating a short-lived permit token is expired at commit time.

TOKEN_REPLAY/ANTI_REPLAY_FAIL. Codes indicating token reuse/replay detected by anti-replay checks.

DEVICE_STATE_UNSAFE. A code indicating the attested device-state vector violates a policy constraint (e.g., temperature threshold exceeded, self-test failed).

CACHE_STALE. A code indicating cached policy is outside its freshness window.

Idempotency key. A value used to suppress duplicate attempts or repeated side effects for the same request/episode under policy.

retry_after_ms. A value indicating a suggested backoff interval before retrying, used in HOLD or retriable denial responses.

J. Miscellaneous Clarifiers

Finalized to the user-interface. Completed to the point that the content is presented to a clinician or otherwise becomes clinically actionable within the device UI context; includes partial finalization of an AI output region.

Clinically actionable. Capable of influencing clinical decisions, actions, or device behavior, including via display, alerting, overlays, or recommended settings.

On or adjacent to the bedside device. Executing on the device, in a device-hosted OS service/hypervisor, in a connected device-adjacent controller, or in a tightly coupled edge node, provided the UI finalization gate semantics are enforced.

Interception. Capturing, mediating, redirecting, gating, or otherwise controlling an inference request or UI finalization event prior to user-visible commitment, using hooks, middleware, drivers, privileged APIs, or equivalents.

Summary/content hash. A representation of AI output included in a receipt, which may include full text, redacted content, a digest, a structured summary, or equivalent representations that support later audit under policy.

Design-around resistance. The specification's repeated definition of "UI finalization gate" as any user-visible commit boundary and the separation of policy admission from any specific symbol/glyph/rendering dictionary implementation enables broad coverage across UI stacks and prevents narrow implementation lock-in.

Appendix B—Example Bedside Safety Receipt Structure (Conceptual; Evidence-Only; Extensible)

Evidence-only/non-limiting notice. This appendix provides illustrative receipt structures to aid enablement, interoperability, procurement, and audit tooling. Unless a claim expressly recites an appendix element, appendix content is illustrative and does not narrow claim scope; the claims control.

Backward compatibility. Receivers SHOULD ignore unknown keys and MUST NOT deny solely due to absence of optional fields unless an active policy requires a predicate. Example schemas do not define required fields unless a claim expressly recites them.

Namespacing/extensions. Implementations MAY include extensions under a namespaced object (e.g., ext{ }) or vendor prefix (e.g., vnd.<org>.*). Extensions are evidence-only and do not narrow.

Privacy note. Receipts MAY store redacted views, pseudonymized identifiers, or digests rather than raw content. The choice of redaction/representation is policy-driven and does not alter permit-before-action semantics.

Canonicalization (illustrative). When a receipt is hashed/digested, canonicalization MAY use stable field ordering, locale-independent numerics, normalized timestamps, and stable null/empty encodings. Any deterministic scheme yielding reproducible digests is equivalent.

B.1 Receipt High-Level Envelope (Illustrative)

Receipt type/version. A receipt MAY include type and version fields to support schema evolution, without requiring any particular format.

Receipt header (example fields). A receipt MAY include:
(a) receipt_id (globally unique identifier);
(b) issued_at (timestamp);
(c) device_id (device identifier) and optionally device_class;
(d) episode_id (bedside inference episode identifier);
(e) policy_id and/or policy_version and/or policy_epoch (policy identifiers);
(f) ai_model_id and/or ai_model_version and/or model_config_digest;
(g) outcome (permit outcome), and optionally codes[ ](deny/hold/guardrail codes); and
(h) ui_finalized (boolean) and/or finalization_gate_id (commit boundary identifier).

HTI/RCM interop fields (optional; evidence-only). To support interoperability with downstream safety receipt layers and AI-governed billing gates, a receipt MAY additionally include one or more of: (i) framework_profile_id(s), (ii) a receipt signature verifiable using a key identifier (e.g., key_id), (iii) policy_digest and, when present, policy_signature or a policy_evaluation_proof ref, (iv) a status_tuple derived from an anchoring event (e.g., signed_head_id, head_timestamp, staleness_interval), and (v) a request/epi-sode binding digest; inclusion of such fields is optional unless an active policy or a claim expressly recites a predicate.

In some embodiments, framework_profile_id(s) include conformance or badge profile identifiers used by external validators to interpret receipt predicates under a pinned profile version and/or digest, without requiring any particular validator implementation; the claims control.

Minimal vs. enriched receipts. Minimal receipts MAY encode a subset of fields sufficient to support audit, while enriched receipts MAY include additional diagnostics (latencies, counters, proofs, cross-rail references).

B.2 Governance Inputs Snapshot (Illustrative)

ADS snapshot. A receipt MAY include ads{ }containing an attested device-state vector snapshot (or digest thereof), such as:
power_state (AC/DC, battery SOC thresholds);
temperature_state;
integrity_state (secure boot/TEE attestation indicators);
self_test_state/calibration_state;
degraded_flags[ ];
ads_digest (optional digest).

CCE snapshot. A receipt MAY include cce{ }containing a clinical context envelope (or digest), such as:
encounter_id and/or order_id and/or episode binding_id;
care_location;
patient_ref (pseudonymized/hashed patient identifier);
modality/acq_params;
timestamps/sequence_id;
cce_digest (optional digest);
encounter_time_window (optional; start/end timestamps or equivalent);
service_type (optional; a service/procedure/class label consistent with a billed service).
Service_binding_commitment (optional; evidence-only). A receipt MAY include a
service_binding_commitment computed as a cryptographic digest over a canonical tuple comprising at least: patient_ref, encounter_id or encounter_time_window, service_type, and episode_id (and optionally order_id and device_id), enabling downstream authorization-to-claim binding rails and revenue-cycle coherence rails to correlate the bedside safety receipt to claim line items without requiring disclosure of direct identifiers.

CIT snapshot. A receipt MAY include cit{ }containing clinician identity information (or digest), such as:
clinician_ref (opaque id);
role/privilege;
auth_method (badge/login/biometric);
cit_digest (optional digest);
encounter_time_window (optional; start/end timestamps or equivalent);
service_type (optional; a service/procedure/class label consistent with a billed service);
Provenance and idempotency (optional; evidence-only). A receipt MAY include (i) a context_field_list and a context_field_list digest computed over a canonicalized representation of the listed context fields used for the permit decision, enabling later recomputation and verification, and (ii) an idempotency_key or commit_marker supporting atomic finalization across retries, without requiring any particular transaction, WAL, or storage mechanism.

B.3 Decision Context and Outcomes (Illustrative)

Permit outcome. A receipt MAY encode outcome E {PERMIT, PERMIT_WITH_GUARDRAILS, REQUIRE_OVERRIDE, HOLD, DENY}(illustrative) and MAY include codes[ ] describing reasons, constraints, or failure predicates, where REQUIRE_OVERRIDE denotes that an explicit override attestation or supervisory confirmation is required prior to finalization, and HOLD denotes a retriable deficit posture under policy.

Guardrails and constraints. A receipt MAY include guardrails[ ] describing applied constraints (e.g., suppress risk scores, warnings, required dual-ack), where guardrails are policy-driven and do not narrow.

Override and acknowledgments. A receipt MAY include clinician_response{ }capturing one or more of:
response ∈ {ACCEPTED, OVERRIDDEN, IGNORED, OTHER};
override_ref (if an override was invoked);
ack_required/ack_observed;
supervisor_ref (optional), and timestamps.

B.4 Timing, Watchdog Budgets, and Latency (Illustrative)
Decision time budget (optional). In watchdog embodiments, receipts MAY include:
decision_time_budget_ms (configured T_ms);
decision_latency_ms (observed latency);
start_marker (e.g., inference start event id); and
time_budget_exceeded (boolean) or a code (TIME_BUD-GET_EXCEEDED).

Event timestamps. Receipts MAY include timestamps for:
request intercept;
ISA generation/verification;
permit evaluation start/end;
UI finalization attempted;
UI finalization committed;
clinician response captured.

B.5 Inference-Start Attestation (ISA) (Optional; Evidence-Only Overlay)
ISA references. Receipts MAY include isa_ref and/or isa_digest and/or a compact ISA summary containing:
episode_id binding;
integrity indicator(s);
model/config digests;
monotonic counter;
signature/MAC reference.
ISA inclusion is optional unless claims recite it.

B.6 Short-Lived Permit Token (SLPT) (Optional; Evidence-Only Overlay)
Token references. In tokenized embodiments, receipts MAY include:
slpt_id and/or slpt_digest;
slpt_exp_ts or slpt_ttl_ms;
anti_replay_summary (e.g., counter or nonce digest);
without disclosing raw token contents.

Commit scope. A receipt MAY include ui_commit_scope and/or finalization_gate_id indicating where finalization was authorized/denied.

B.7 Tamper Evidence/Anchoring (Optional; Evidence-Only Overlay)
Signature. A receipt MAY include signature (or receipt_sig) over at least a subset of fields, and MAY include key identifiers and trust domain identifiers.

Anchoring. A receipt MAY include anchor_ref describing anchoring to a tamper-evident store/log, such as:
store_id/log_id/structure id (illustrative);
entry_id or inclusion_ref;
head_id (optional);
proof refs{ }(optional).
Anchoring remains evidence-only unless claims recite it.

B.8 Cross-Rail References (Evidence-Only; Non-Limiting)
Cross-rail references. Receipts MAY include cross_rail_references[ ] referencing other governance receipts (sensor receipts, safety evidence receipts, revenue-cycle receipts), using opaque ids/digests/pointers, without requiring any particular rail.

In some embodiments, cross_rail_references include, as evidentiary-only entries, identifiers or digests of authorization-to-claim binding receipts (e.g., ATR/CTR) and/or billing-governance receipts that bind at least a safety receipt identifier, an evaluated permit outcome, and a billing disposition, without altering BAPR gate semantics.

B.9 Example Receipt Object (Illustrative JSON; Evidence-Only)

Example (non-limiting; fields optional unless recited by claims):

```
{
    "type": "BedsideSafetyReceipt",
    "version": "1.0",
    "receipt_id": "bsr:. . .",
    "issued_at": "2026-01-01T00:00:00Z",
    "device": {"device_id": "dev:. . .", "device_class":
        "ultrasound|monitorl . . . " },
    "episode_id": "ep:. . .",
    "policy": {"policy_id": "pol:. . .", "policy_version":
        "v:. . .", "policy_epoch": "epoch:. . ." },
    "model": {"ai_model_id": "mdl:. . .", "ai_model_ver-
        sion":        "1.2.3",        "model_config_digest":
        "sha256:. . ." },
    "ads": {"ads_digest": "sha256:. . .", "power_state":
        "AC", "battery_soc": 0.82, "temperature_c": 41.0,
        "integrity_state": "tee_ok", "self_test_state": "pass",
        "degraded flags": [ ]},
"cce": {
    "encounter_id": "enc:. . .",
    "order_id": "ord:. . .",
    "care_location": "ICU",
    "patient_ref": "pt:hash:. . .",
    "modality": "ECG",
    "encounter_time_window":        {"start":".      .      .      ",
        "end":" . . . " },
    "service_type":"POCUS_MEASUREMENT"
},
    "cit": {"clinician_ref": "cln:. . .", "role": "attending",
        "auth_method": "badge tap" },
    "decision": {"outcome": "PERMIT_WITH_GUARD-
        RAILS", "codes": [ ], "guardrails": ["SUP-
        PRESS_RISK_SCORE","WARNINGS_RE-
        QUIRED" ]},
"ui": {"ui_finalized": true, "finalization_gate_id": "ui:
    commit:. . .", "ui_commit_scope":
"ui:region:AI_PANEL" },
    "consent": {
    "consent_ref": "consent:. . .",
    "consent_digest": "sha256:. . .",
    "consent_time_anchor": "2026-01-01T00:00:00Z",
    "consent_scope": "episodelorderlprocedure",
    "consent_latch_satisfied": true
},
"timing":        {"decision_time_budget_ms":        150,
    "decision_latency    ms":    87,    "timestamps":
    {"request": " . . . ", "permit end": " . . . ", "ui_
    commit": " . . . }},
"isa": {"isa_digest": "sha256:. . ." },
"slpt":  {"slpt_digest": "sha256:.  .  .", "slpt_exp_ts":
    "2026-01-01T00:00:01Z" },
"clinician_response":    {"response":    "ACCEPTED",
    "response_ts": " . . . " }
"degraded_state_flag": false,
```

"cross_rail_references": ["tsil:sr:. . .", "srbe:ser:. . ." ],
"interop": {
    "framework_profile_ids": ["FW:HTI1:. . .", "CB-EDGE-1:v1" ],
    "policy_digest": "sha256:. . .",
    "policy_signature": "sig:. . .",
    "receipt_key_id": "kid:. . .",
    "receipt_signature": "sig:. . ."
},
    "provenance": {"context_field_list digest": "sha256:. . .", "idempotency_key": "idem:. . ." },
    "signature": "sig:. . .",
    "anchor_ref": {"store_id": "log:. . .", "entry_id": "e:. . ." },
    "ext": {
}

Appendix C—Deny/Hold Codes (Evidence-Only; Non-Exhaustive; Interoperable)

Evidence-only/non-limiting notice. Codes standardize machine-readable outcomes and do not define or limit claim scope. Policies MAY map selected codes to HOLD vs DENY; default behavior is DENY unless configured.

Retryability. A code MAY be designated retriable when remediation is possible (e.g., refresh policy cache, re-obtain attestation, request new token). When retriable, responders SHOULD include retry_after_ms and MAY include idempotency_key.

Extensibility and aliases. Implementations MAY add namespaced variants (e.g., vnd.<org>.<code>). Unknown codes SHOULD NOT break clients. Aliases MAY map to functionally equivalent semantics (see [0276]).

Code packaging. A denial/hold response MAY include: status ∈ {HOLD,DENY}, codes[ ], retry_after_ms, idempotency_key, and an evidence pointer to a receipt or decision record.

C.1 Timing/Watchdog/Backpressure
TIME_BUDGET_EXCEEDED—permit evaluation exceeded configured decision time budget; fail—closed.
POLICY_EVAL_TIMEOUT—policy evaluation exceeded allowed time slice.
ADMISSION_BUSY—gate busy; backoff suggested.
RATE_LIMIT—admission rate exceeded; backoff suggested.
CLOCK_UNTRUSTED—timer source untrusted/invalid for time-bound operation (optional).
C.2 Inference-Start Attestation/Integrity
START_ATTEST_REQUIRED—ISA required by policy and missing.
START_ATTEST_FAIL—ISA present but invalid/unverifiable/inconsistent.
INTEGRITY_REQUIRED—integrity indicator required and missing.
INTEGRITY_FAIL—integrity indicator indicates unsafe or untrusted state.
ATTESTATION_FAIL—remote attestation report invalid/untrusted.
C.3 Token/Anti-Replay/Commit-Time Authorization
TOKEN_REQUIRED—UI finalization attempted without required permit token.
TOKEN_EXPIRED—token expired at commit time.
TOKEN_REPLAY—token reuse detected for episode/scope.
ANTI_REPLAY_FAIL—nonce/counter/epoch replay detected.
TOKEN_SCOPE_MISMATCH—token not bound to observed UI commit scope.

TOKEN_SIGNATURE_INVALID—token signature/MAC invalid.
C.4 Device-State/Safety Constraints
DEVICE_STATE_UNSAFE—ADS violates policy constraint (temperature, power, integrity, self-test, calibration).
SELF_TEST_REQUIRED—required self-test/calibration predicate missing.
SENSOR_UNAVAILABLE—required sensor data unavailable.
DEGRADED_MODE_FORCED—degraded state forces HOLD/DENY under policy.
C.5 Identity/Role/Control
IDENTITY_REQUIRED—clinician identity token required and missing.
IDENTITY_UNTRUSTED—identity unverifiable/untrusted.
ROLE_MISMATCH—role/privilege insufficient for requested action.
SUPERVISOR_REQUIRED—supervisory confirmation required and missing.
OVERRIDE_NOT_AUTHORIZED—override attempted without authorization.
C.6 Context/Required Fields
CONTEXT_REQUIRED—CCE/episode binding required and missing.
REQUIRED_FIELD_MISSING—required field absent (policy-designated).
REQUIRED_FIELD_MALFORMED—required field present but malformed/unparsable.
EPISODE_BINDING_FAIL—episode/encounter/order binding inconsistent.
C.6A Consent/Authorization
CONSENT_REQUIRED—consent evidence required by policy and missing.
CONSENT_UNVERIFIED—consent present but unverifiable/invalid.
CONSENT_EXPIRED—consent outside effective window at commit time.
CONSENT_REVOKED—consent revoked/rescinded for applicable scope.
CONSENT_SCOPE_MISMATCH—consent scope inconsistent with episode/order/procedure or UI commit scope.
CONSENT_REPLAY—reused consent binding detected across episodes/scopes where policy forbids reuse.
C.7 Policy/Cache/Freshness
POLICY_REQUIRED—policy identifier/context required and missing.
POLICY_DENIED—evaluation failed for non-retriable predicate.
CACHE_STALE—cached policy outside freshness window.
POLICY_EPOCH_MISMATCH—incompatible policy epoch/version (downgrade resistance).
POLICY_FETCH_FAIL—policy fetch/validation failed.
C.8 UI Enforcement/Finalization Integrity
FINALIZATION_BLOCKED—UI finalization blocked by gate per policy.
FINALIZATION_RACE_DETECTED—attempted finalization prior to PASS (TOCTOU).
UI_GATE_UNAVAILABLE—UI finalization gate unavailable/unverifiable.
C.9 Anchoring/Audit (Optional; Evidence-Only)
SIGNATURE_INVALID—receipt/decision signature invalid.
ANCHOR_FAIL—anchoring attempted and failed (if configured).

AUDIT_POINTER_REQUIRED—audit pointer required by policy and missing.

C.99 Aliases & Compatibility (Non-Normative; Evidence-Only)

Illustrative equivalences (non-limiting):
LATCH_TIMEOUT≡TIME_BUDGET_EXCEEDED
TOKEN_MISSING≡TOKEN_REQUIRED
REPLAY_DETECTED≡TOKEN_REPLAY or ANTI-_REPLAY_FAIL
POLICY_STALE≡CACHE_STALE
TEE_FAIL≡ATTESTATION_FAIL Appendix D—Schema Stubs (Evidence-Only; Extensible; Hard-to-Design-Around)

Evidence-only/non-limiting notice. Schemas are illustrative and transport-neutral. Only predicates recited by claims are required; all other fields are optional. Encodings may be JSON, CBOR, Protobuf, database rows, or equivalents. The following code blocks are JSON-like for readability; inline comments (e.g., // . . . ) are explanatory and may be removed for strict JSON compliance.

Unknown keys. Receivers SHOULD ignore unknown keys and MUST NOT deny solely due to absence of optional fields unless policy requires a predicate.

Canonical digests (optional). When digests are used, any deterministic canonicalization yielding reproducible digests is equivalent.

Extensibility. Each object MAY include ext{ } for namespaced extensions; extensions do not narrow claim scope.

D.1 Short-Lived Permit Token (SLPT) (Illustrative)

SLPT is an authorization artifact used at commit time in tokenized embodiments. Fields are illustrative:

```
{
    "type": "SLPT",
    "version": "1.0",
    "token_id": "slpt:. . .",
    "episode_id": "ep:. . .",
    "isa_digest": "sha256:. . .", // optional binding to
        inference-start attestation
    "policy_id": "pol:. . .",
    "policy_epoch": "epoch:. . .", // optional
    "ui_commit_scope": "ui:region:. . . |ui:session:. . .
        |ui:commit:. . .",
    "exp_ts": "2026-01-01T00:00:01Z", / or ttl_ms
    "ttl_ms": 1000, / optional alternative to exp_ts
    "anti_replay": {"nonce": " . . . ", "counter": 123,
        "epoch": "epoch:. . ." },
    "signature": "sig:. . .", // or mac
    "key_id": "kid:. . .", // optional
    "ext": {
}
```

D.2 Inference-Start Attestation (ISA) (Illustrative)

ISA binds permit evaluation to a verifiable inference start event. Fields are illustrative:

```
{
    "type": "ISA",
    "version": "1.0",
    "isa_id": "isa:. . .",
    "episode_id": "ep:. . .",
    "model": {"ai_model_id": "mdl:. . .", "ai_model_ver-
        sion": "1.2.3", "model_config_digest":
        "sha256:. . ." },
    "integrity": {
        "secure_boot_digest": "sha256:. . .",
        "tee_report_ref": "tee:rep:. . .",
        "integrity_indicator": "tee_ok|sb_okj . . . "
},
```

```
    "counter": 456,
    "ts": "2026-01-01T00:00:00Z",
    "signature": "sig:. . .",
    "ext": {
}
```

D.3 Bedside Safety Receipt (Enriched) (Illustrative)

Full receipt stub (illustrative; any subset may be used unless required by claim/policy):

```
{
    "type": "BedsideSafetyReceipt",
    "version": "1.0",
    "receipt_id": "bsr:. . .",
    "issued_at": "2026-01-01T00:00:00Z",
    "device": {"device_id": "dev:. . .", "device_class":
        "monitor|ultrasound| . . . ", "device_sw_digest":
        "sha256:. . ." },
    "episode_id": "ep:. . .",
    "cce": {"encounter_id": "enc:. . .", "order_id":
        "ord:. . .", "care_location": "ICU", "patient_ref":
        "pt:hash:. . .", "cce_digest": "sha256:. . ." },
    "cit": {"clinician_ref": "cln:. . .", "role": "attending",
        "auth_method": "badge tap", "cit_digest":
        "sha256:. . ." },
    "ads": {"ads_digest": "sha256:. . .", "power_state":
        "AC", "battery_soc": 0.82, "temperature_c": 41.0,
        "integrity_state": "tee_ok", "self_test_state": "pass",
        "degraded flags": [ ]},
    "policy": {"policy_id": "pol:. . .", "policy_version":
        "v:. . .", "policy_epoch": "epoch:. . ." },
    "decision": {
    "outcome": "PERMIT|PERMIT_WITH_GUARD-
        RAILS|HOLD|DENY",
    "codes": [" . . . " ],
    "guardrails": [" . . . " ],
    "decision_id": "dec:. . ."
},
"ui": {"ui_finalized": true, "finalization_gate_id": "ui:
    commit:. . .", "ui_commit_scope":
"ui:region:AI_PANEL" },
    "consent": {
    "consent_ref": "consent:. . .",
    "consent_digest": "sha256:. . .",
    "consent_time_anchor": "2026-01-01T00:00:00Z",
    "consent_scope": "episode|order|procedure",
    "consent_latch_satisfied": true
},
"timing": {
    "decision_time_budget ms": 150,
    "decision_latency_ms": 87,
    "timestamps": {"request": " . . . ", "permit
        start": " . . . ", "permit end": " . . . ", "ui_commit" "
    "response": " . . . " }
},
"isa": {"isa_digest": "sha256:. . ." },
"slpt": {"slpt_digest": "sha256:. . .", "slpt_exp_ts":
    "2026-01-01T00:00:01Z" },
"ai_output": {"summary": "optional", "output digest":
    "sha256:. . .", "confidence": 0.92}
"clinician_response": {"response": "ACCEPTED|O-
    VERRIDDEN|IGNORED|OTHER", "response_
    ts": " . . . " },
"degraded_state_flag": false,
"cross_rail_references": ["tsil:sr:. . .", "srbe:ser:. . .",
    "trc:rctr:. . ." ],
"signature": "sig:. . .",
"anchor_ref": {"store_id": "log:. . .", "entry_id":
    "e:. . ." },
```

```
    "ext": {
    }
```

D.4 Receipt Delta (Minimal Addendum Fields) (Illustrative)

Minimal "delta" fields for watchdog/token/ISA embodiments (illustrative):

```
    {
      "isa_digest": "sha256:. . .",
      "decision_time_budget_ms": 150,
      "decision_latency_ms": 87,
      "slpt_digest": "sha256:. . .",
      "codes":
    ["TIME_BUDGET_EXCEEDED|TOKEN_EXPIRED|
    TOKEN_REPLAY|START_ATTEST_FA
      "ui_finalized": true
    }
```

D.5 Structured Precondition Failure (SP-F) Style Response (Optional; Evidence-Only)

Some embodiments MAY emit a structured denial/hold response (SP-F-like) for programmatic handling; illustrative only:

```
    {
      "type": "SPF",
      "version": "1.0",
      "decision_id": "dec:. . .",
      "status": "HOLD|DENY",
      "codes": [" . . . " ],
      "retry_after_ms": 200,
      "idempotency_key": "idem:. . .",
      "context": {"episode_id": "ep:. . .", "policy_id": "pol:.
        . .", "finalization_gate_id":
      "ui:commit:. . ." },
      "deny_signature": "sig:. . .",
      "ext": {
    }
```

Appendix E—Conformance, Certification, Procurement, and SDK Artifacts (Evidence-Only; Non-Limiting)

Evidence-only/non-limiting notice. This appendix provides illustrative conformance artifacts, test vectors, and interface stubs to improve enablement, interoperability, procurement clarity, and audit tooling. Unless a claim expressly recites an appendix element, appendix content is illustrative and does not narrow claim scope; the claims control.

No additional predicates. These artifacts do not introduce new gating predicates or modify permit-before-action semantics. The core nucleus remains: UI finalization is admitted only after policy evaluation over governance inputs (ADS/CCE/CIT and optional ISA), enforced at a UI finalization gate with fail-closed behavior.

Backward compatibility. Receivers SHOULD ignore unknown keys and MUST NOT deny solely due to absence of optional fields unless an active policy requires a predicate. Profiles and manifests are evidence-only and do not define required claim elements.

Transport neutrality. Any schemas or interfaces may be encoded as JSON, CBOR, Protobuf, database rows, gRPC, REST, IPC calls, driver APIs, or equivalents.

E.1 Conformance Manifest (Evidence-Only)

Purpose. A deployment MAY publish a Conformance-Manifest to help integrators and procurement teams understand supported features (e.g., watchdog latch, tokens, ISA), supported attestations, UI gate placement options, and denial taxonomy behavior.

Non-dispositive. The presence or absence of a Confor-manceManifest does not alter claim scope. Feature flags are descriptive only.

ConformanceManifest fields (illustrative). A Confor-manceManifest MAY include:

(a) manifest_id, manifest_version, issued_at;

(b) profile_id/profile_version (evidence-only profile name);

(c) supports_watchdog (boolean), default_decision_time_budget_ms (optional);

(d) supports_slpt (boolean), token_ttl_bounds_ms (optional), anti_replay_modes[ ](optional);

(e) supports_isa (boolean), isa_sources[ ](TEE, secure boot, signed manifest) (optional);

(f) ui_finalization_gate_types[ ](composition hook, driver commit hook, framebuffer boundary, UI service gateway, etc.);

(g) attestation_types[ ](TEE report, secure boot measurement, signed firmware manifest, calibration attestation);

(h) deny_taxonomy_id (evidence-only reference to a code mapping);

(i) receipt_min_fields (illustrative guidance only; not required unless policy/claims recite);

(j) privacy_modes[ ](digest-only, redacted view, pseudonymization);

(k) retention_windows (receipt buffer window, denial retention) (evidence-only); and (l) signature and optional key_id.

Illustrative ConformanceManifest (JSON; evidence-only).

```
    {
      "type": "ConformanceManifest",
      "version": "1.0",
      "manifest_id": "cm:. . .",
      "issued_at": "2026-01-01T00:00:00Z",
      "profile": {"profile_id": "BAPR-CORE", "profile_ver-
        sion": "v1" },
      "features": {
        "supports_watchdog": true,
        "default_decision_time_budget_ms": 150,
        "supports_slpt": true,
        "token_ttl_bounds_ms": [100, 5000],
        "anti_replay_modes":    ["nonce",    "counter",
          "epoch" ],
        "supports_isa": true,
        "isa_sources": ["tee_report", "secure_boot_digest" ]
      },
      "ui_finalization_gate_types":    ["ui_commit_hook",
        "composition_layer",
    "driver_commit_hook", "framebuffer_boundary" ],
        "attestation_types": ["tee_attestation", "secure_boot",
          "signed_manifest", "calibration_state" ],
        "deny_taxonomy_id": "BAPR-DENY-CODES-1.0",
        "privacy_modes":   ["digest_only",   "pseudonymize-
          d_refs", "redacted_views" ],
        "signature": "sig:. . .",
        "ext": {
    }
```

E.2 Certification Result/Receipt Index (Evidence-Only)

Purpose. A verifier, operator, OEM, or hospital MAY maintain a signed index to support audits and reproducible replay of "what policy and gate semantics were applied" for a given episode.

Non-dispositive. Certification artifacts are evidence-only and do not alter claim scope. Certification may be internal, third-party, automated, manual, or hybrid.

SignedReceiptIndex (illustrative). A SignedReceiptIndex MAY be keyed by episode_id and/or receipt_id and MAY store:

(a) receipt digest;

(b) policy_id/policy_epoch;

(c) finalization_gate_id/ui_commit_scope (optional);

(d) isa_digest (optional);

(e) slpt_digest (optional);

(f) codes[ ](optional);

(g) signature and issuance timestamp.

Illustrative SignedReceiptIndex entry (JSON; evidence-only).

```
{
    "type": "SignedReceiptIndexEntry",
    "version": "1.0",
    "episode_id": "ep:. . .",
    "receipt_id": "bsr:. . .",
    "receipt_digest": "sha256:. . .",
    "policy_id": "pol:. . .",
    "policy_epoch": "epoch:. . .",
    "finalization_gate_id": "ui:commit:. . .",
    "isa_digest": "sha256:. . .",
    "slpt_digest": "sha256:. . .",
    "codes": [ ],
    "issued_at": "2026-01-01T00:00:02Z",
    "signature": "sig:. . .",
    "ext": {
    }
}
```

Revocation/rescission (optional; evidence-only). An operator MAY publish a signed rescission record when a certification assertion is withdrawn; such records do not alter gating semantics.

E.3 Conformance Test Vectors (Evidence-Only; Non-Limiting)

Purpose. Test vectors help validate interoperability and expected permit/deny behavior for the BAPR nucleus across implementations.

Non-limiting. Inputs/outputs below are illustrative. Equivalent test structures are within scope. Passing a test vector is not a claim limitation.

Vector format (illustrative). Each vector MAY specify: Inputs, Policy predicates, Expected outcome, Expected codes, Expected receipt fields (optional), and Notes.

E.3.1 Minimal PASS

Inputs: Valid ADS; valid CCE; valid CIT; policy permits.

Expected: PERMIT or PERMIT_WITH_GUARD-RAILS; UI finalization occurs.

Codes: none required.

Receipt (optional): outcome, policy_id, device_id, episode_id, timing.

E.3.2 Device_state_unsafe

Inputs: ADS indicates temperature threshold exceeded OR self-test failed.

Expected: DENY (or HOLD per policy mapping); UI finalization blocked; safe-mode overlay optional.

Codes: DEVICE_STATE_UNSAFE (or equivalent).

E.3.3 Identity untrusted

Inputs: CIT missing/invalid/unverifiable.

Expected: DENY; UI finalization blocked.

Codes: IDENTITY_REQUIRED or IDENTITY_UN-TRUSTED.

E.3.4 Context Required

Inputs: Missing encounter/order binding when policy requires.

Expected: DENY or HOLD; UI finalization blocked.

Codes: CONTEXT_REQUIRED or REQUIRED_FIELD_MISSING.

E.3.5 Cache Stale (Offline/Degraded)

Inputs: Connectivity loss; cached policy outside freshness window.

Expected: HOLD or DENY per policy; UI finalization blocked; degraded_state_flag true.

Codes: CACHE_STALE and/or DEGRADED_MODE_FORCED.

E.3.6 Watchdog time budget exceeded (if watchdog enabled)

Inputs: Permit evaluation does not complete within decision_time_budget_ms.

Expected: fail-closed HOLD/DENY; UI finalization blocked.

Codes: TIME_BUDGET_EXCEEDED (or equivalent).

Receipt (optional): decision_time_budget_ms, decision_latency_ms, ui_finalized=false.

E.3.7 ISA Required but Missing (if ISA Enabled and Policy Requires)

Inputs: Policy requires ISA; ISA missing.

Expected: DENY; UI finalization blocked.

Codes: START_ATTEST_REQUIRED (or equivalent).

E.3.8 ISA Fails Verification

Inputs: ISA present but integrity indicator fails or signature invalid.

Expected: DENY or HOLD; UI finalization blocked.

Codes: START_ATTEST_FAIL and/or INTEGRITY_FAIL.

E.3.9 Token Required but Missing (if SLPT Enabled)

Inputs: Tokenized commit required; UI finalization attempted without SLPT.

Expected: DENY; UI finalization blocked.

Codes: TOKEN_REQUIRED.

E.3.10 Token expired at commit time (if SLPT enabled)

Inputs: SLPT present but expired at commit.

Expected: DENY; UI finalization blocked.

Codes: TOKEN_EXPIRED.

E.3.11 Token Replay (if SLPT Enabled)

Inputs: SLPT reused for different episode/scope or reused after commit.

Expected: DENY or HOLD; UI finalization blocked.

Codes: TOKEN_REPLAY and/or ANTI_REPLAY_FAIL.

E.3.12 Guardrail Permit

Inputs: Policy returns PERMIT_WITH_GUARDRAILS.

Expected: UI finalization allowed subject to constraints.

Codes: may include guardrail descriptors (evidence-only).

Receipt: guardrails[ ] optionally includes constraints applied.

E.3.13 Authorized Override Flow (Policy-Governed)

Inputs: Initial non-permit; authorized clinician performs override action.

Expected: UI finalization allowed only after override is recorded; receipt records override.

Codes: may include OVERRIDE_USED (evidence-only) or response field indicates override.

E.4 Procurement/Vendor Evaluation Checklist (Evidence-Only; Non-Limiting)

Purpose. A non-limiting checklist for hospitals/OEMs to evaluate whether an implementation provides robust BAPR semantics. This checklist is evidence-only and does not narrow scope.

Critical-path enforcement (core).

(a) Is there a verifiable UI finalization gate in the critical path (composition/driver/framebuffer/IPC or equivalent)?

(b) Does the implementation enforce ui_finalized ⇒ PASS under load and partial failure?

(c) Does it prevent "late permit" or "partial verification" finalization?

Governance inputs (core).

(a) Device-state attestation: integrity+safety indicators captured (power/temp/self-test/calibration).

(b) Clinical context binding: episode/encounter/order+ location; patient ref handled per privacy.

(c) Clinician identity: authenticated identity+role/privilege where relevant.

Fail-closed and degraded modes (core).

(a) When policy cache is stale or attestation cannot complete, does it default to HOLD/DENY?

(b) Can non-AI device functions continue while AI output is withheld?

(c) Are degraded episodes recorded in receipts?

Watchdog time-bounds (optional moat).

(a) Can a decision time budget be configured per workflow?

(b) Is TIME_BUDGET_EXCEEDED handled failclosed?

(c) Are latency metrics captured (decision_latency_ms)?

Tokenized commit (optional moat).

(a) Is UI finalization gated at commit time by a short-lived permit token?

(b) Are TTL+anti-replay enforced (TOKEN_EXPIRED/ TOKEN_REPLAY/ANTI_REPLAY_FAIL)?

(c) Is token scope bound to episode and UI commit scope?

Receipts (core).

(a) Are receipts structured and machine-readable?

(b) Do receipts include outcome+policy_id/version+episode_id+device_id?

(c) Do receipts record clinician response (accept/override/ ignore) when available?

Tamper evidence (optional overlay).

(a) Are receipts signed?

(b) Is optional anchoring supported without coupling to a specific log vendor/format?

Interoperability and privacy (upgrade).

(a) Unknown keys ignored; optional fields not required by default.

(b) Supports pseudonymized identifiers and digest-only modes.

(c) Provides cross-rail references without forcing dependencies.

Security posture (upgrade).

(a) Protects against bypass of UI gate.

(b) Controls replay and reuse of permits/tokens (if enabled).

(c) Provides auditable evidence for denied finalization attempts (optional).

E.5 Mini SDK Interface (Evidence-Only; Transport-Neutral)

Purpose. A minimal interface stub enabling integrators to implement BAPR semantics consistently across OS/app/ firmware boundaries. Evidence-only; does not narrow claim scope.

Non-dispositive interface notice. Any particular API name, signature, field, or wire format is illustrative. Functionally equivalent interfaces producing the same PASS/ HOLD/DENY semantics are within scope.

E.5.1 Core Interfaces (Illustrative)

EvaluatePermit (core): Evaluate policy over governance inputs and return a decision. Input (illustrative): episode_id, ads, cce, cit, optional isa, optional policy_hint.

Output (illustrative):

decision{outcome,codes[ ],guardrails[ ],policy_id,policy_epoch,decision_id,decision_latency_ms}.

FinalizeGateCheck (core): Called at UI finalization gate prior to commit.

Input: decision_id (or decision snapshot), ui_commit_scope, optional slpt.

Output: allow_commit boolean, optional codes[ ].

EmitReceipt (core): Emit structured bedside safety receipt.

Input: governance snapshots+decision+UI commit result+ clinician response (if any).

Output: receipt_id, receipt digest (optional).

E.5.2 Optional Interfaces (Moat Modules)

GenerateISA (optional): Generate inference-start attestation at inference start. Output: isa{isa_id,isa_digest,. . .}.

StartWatchdog/EnforceBudget (optional): Start watchdog timer and enforce time budget for evaluation and/or commit.

Input: decision_time_budget_ms.

Output: budget_state and/or codes on exceed.

IssueSLPT (optional): Issue short-lived permit token on PASS.

Output: slpt{slpt_id,slpt_digest,exp_ts,anti_replay_summary}.

VerifySLPT (optional): Verify token at commit time including TTL and anti-replay.

Output: valid boolean, codes on failure.

E.5.3 Illustrative SDK Pseudocode (Evidence-Only)

```
on_inference_request(req):
  isa=optional GenerateISA(req)
  start=now_monotonico
  decision=EvaluatePermit(episode_id, ads, cce, cit, isa)
  if    watchdog_enabled    and    (now_monotonico-
      start >T_ms):
    decision.outcome=HOLD    or    DENY,    decision.
        codes+=TIME_BUDGET_EXCEEDED          if
        decision.outcome is PERMIT:
    slpt=optional    IssueSLPT(decision,    episode_id,
        ui_commit_scope, TTL) return decision, slpt
  on_ui_finalization_attempt(ui_event):
    (allow,    codes)=FinalizeGateCheck(decision_id,
        ui_commit_scope, slpt)
    if not allow: render SafeModeOverlay; record codes
    EmitReceipt(. . . , ui_finalized=allow, codes=codes)
    if allow: commit to uio
```

E.6 Functional Equivalents and Non-Narrowing Notes (Evidence-Only)

Equivalents Conformance manifests, indices, test vectors, and SDK interfaces include functionally equivalent mechanisms that achieve the same permit-before-action admission semantics and fail-closed behavior.

Non-requirement. Nothing in this appendix requires a particular dictionary-based rendering system, visibility mask, GPU DFA, or symbol grammar mechanism; UI finalization gating may be implemented using any equivalent commit boundary control.

Acceptance criteria (evidence-only; non-limiting). An implementation is considered conformant, in an illustrative sense, when it (i) enforces a UI finalization gate such that ui_finalized ⇒PASS, (ii) fails closed under missing/invalid ADS/CCE/CIT predicates required by policy, (iii) records a structured bedside safety receipt containing at least episode_id, outcome, policy identifier, and device identifier, and (iv) preserves backward compatibility by ignoring unknown keys and not denying solely due to absence of optional fields unless policy requires a predicate. Optional modules (ISA, watchdog, SLPT) may be validated via corresponding test vectors without being required.

Appendix F—Security/Threat Model and Mitigation Narrative (Evidence-Only; Non-Limiting)

Evidence-only/non-limiting notice. This appendix provides illustrative threat and mitigation narratives to aid enablement, procurement, audit, and risk review. Unless a claim expressly recites an appendix element, appendix content is illustrative and does not narrow claim scope; the claims control.

Nucleus (informative; non-limiting). The BAPR nucleus enforces that AI inference outputs do not become user-visible or clinically actionable unless admitted by policy evaluation over governance inputs (ADS/CCE/CIT and optional ISA), enforced at a user-interface finalization gate with fail-closed behavior. Optional enhancements include watchdog time budgets and short-lived anti-replay permit tokens.

Representation-agnostic enforcement (non-limiting). The disclosed enforcement does not require any particular symbolic rendering pipeline, constrained glyph dictionary, visibility mask, GPU-resident DFA, or vendor-specific graphics mechanism. The UI finalization gate may operate over any output representation (text, raster, vector overlays, UI messages, textures, regions, frames, or equivalents).

Rendering-constraint techniques (informative; non-limiting). For clarity, certain approaches may enforce display-time constraints by mapping AI tokens to constrained symbol or glyph dictionaries prior to pixel emission (including via a graphics-pipeline-resident state machine and/or visibility masking). When used solely as a display-time constraint mechanism and without enforcing permit-before-finalization admission control at a user-interface finalization gate based on governance inputs comprising ADS/CCE/CIT (and, in some embodiments, ISA and/or time-bounded watchdog latching), such approaches do not, by themselves, provide the commit-boundary admission semantics described herein. In the disclosed admission-control approach, user-visible finalization is admitted only upon a permit outcome corresponding to a permit value (PASS) at a user-visible commit boundary. Such rendering-constraint techniques may optionally be used as supplementary guardrails in some embodiments; the claims control.

F.1 Illustrative Threats Addressed by the Nucleus (Narrative)

Bypass/unauthorized UI finalization. A compromised app or inference engine may attempt to finalize AI output without admission (e.g., direct writes into display paths). Mitigation: place the UI finalization gate in the critical path and enforce the invariant ui_finalized $\Rightarrow$PASS, failing closed and optionally rendering a safe-mode overlay.

TOCTOU races. Governance inputs (identity, device state, policy) may change between check and finalization. Mitigation: enforce admission at the commit boundary, optionally re-validate required predicates at commit time, and record the finalization gate identifier and timing in receipts.

Post-hoc consent injection. Consent may be added or altered after an inference episode to justify a previously displayed output. Mitigation: time-of-consent latch+commit-time verification; ambiguous applicability fail-closes.

Consent replay across episodes/scopes. Consent evidence may be reused to authorize unrelated episodes or different UI commit scopes. Mitigation: consent-bound SLPT and scope checks; CONSENT_REPLAY/CONSENT_SCOPE_MISMATCH handling.

Identity/scope mismatch. The consenting party or authorized-agent scope may not match the episode/order context.

Mitigation: policy-evaluable scope bindings in the CCE and commit-time verification with fail-closed behavior.

Identity spoofing/role abuse. An attacker or insider may spoof clinician identity or exceed privileges. Mitigation: require clinician identity token validation and role predicates under policy; record clinician response/override provenance; optionally require dual-ack or supervisory confirmation.

Device integrity compromise/unsafe device conditions. Firmware, configuration, or operating conditions may be unsafe (temperature, power, failed self-test, degraded modes).

Mitigation: include integrity and safety indicators in the attested device-state vector; deny/hold under policy; preserve non-AI device functions while withholding AI output.

Stale policy and offline drift. Cached policy may become stale or unavailable. Mitigation: enforce policy freshness windows; on staleness/unavailability, force degraded behavior that maps to HOLD/DENY and records degraded state in receipts.

Verification under load/latency pressure. An adversary or fault may delay evaluation to induce permissive fallback. Mitigation (optional): a watchdog time budget enforces bounded-latency decisions and fails closed on timeout, preventing "late permit" UI finalization.

Permit/token replay. Permits may be reused across episodes or scopes. Mitigation (optional): short-lived permit tokens with TTL+anti-replay tuples bound to episode identifier and UI commit scope; verify token validity at commit time and deny on replay/expiry.

Receipt tampering/repudiation. Actors may alter or delete records. Mitigation: digitally sign receipts; optionally anchor commitments to a tamper-evident store; store digests/redacted views where appropriate.

Privacy leakage via receipts. Receipts may leak sensitive information. Mitigation: digest-only or redacted representations; pseudonymized patient references; policy-driven minimization; avoid storing raw content unless required.

Training data poisoning via unsafe episodes. Unsafe/degraded episodes may enter training sets. Mitigation: gate training admission using receipt predicates (permit outcome, no degraded state, integrity OK) and exclude HOLD/DENY episodes.

F.2 Illustrative Codes/Signals (Evidence-Only)

Example codes (non-exhaustive) include: TIME_BUDGET_EXCEEDED, POLICY_EVAL_TIMEOUT, START_ATTEST_FAIL, TOKEN_REQUIRED, TOKEN_EXPIRED, TOKEN_REPLAY, ANTI_REPLAY_FAIL, DEVICE_STATE_UNSAFE, IDENTITY_UNTRUSTED, CACHE_STALE, ATTESTATION_FAIL, FINALIZATION_RACE_DETECTED. Code taxonomies are evidence-only and do not narrow claim scope.

The invention claimed is:

1. A bedside clinical device comprising one or more processors and memory storing instructions that, when executed by the one or more processors, cause the bedside clinical device to:

(a) host or access an AI inference engine configured to generate an AI inference output for a bedside inference episode;

(b) receive or intercept, by a bedside AI permit rail, at least one of: (i) an inference request or (ii) a user-interface finalization request associated with the bedside inference episode;

(c) obtain an attested device-state vector for the bedside clinical device, the attested device-state vector comprising one or more indicators including at least one indicator selected from: a power or energy state indicator, a temperature indicator, or a software or firmware integrity indicator of the bedside clinical device;

(d) obtain a clinical context envelope for the bedside inference episode, the clinical context envelope comprising (i) one or more identifiers of at least a clinical episode, encounter, or order and (ii) a care location;

(e) obtain a clinician identity token indicating an authenticated clinician and at least one role or privilege attribute associated with the bedside inference episode;

(f) evaluate, by a policy evaluator, a policy graph based at least on the attested device-state vector, the clinical context envelope, and the clinician identity token to compute a permit outcome selected from a plurality of enumerated outcomes comprising at least a permit value and a non-permit value;

(g) enforce a permit-before-finalization configuration by controlling a user interface of the bedside clinical device at a user-interface finalization gate corresponding to a commit boundary at which the AI inference output becomes user-visible or clinically actionable, such that the AI inference output is prevented from being finalized to the user interface for the bedside inference episode unless the permit outcome corresponds to the permit value among the enumerated outcomes;

(h) generate, for the bedside inference episode, a structured bedside safety receipt encoding at least the attested device-state vector, the clinical context envelope, the clinician identity token, a policy identifier and at least one of a policy_version identifier, a policy digest, or a policy epoch associated with the policy graph, the permit outcome, and a summary or digest of the AI inference output.

2. The bedside clinical device of claim 1, wherein the plurality of enumerated outcomes further comprises REQUIRE_OVERRIDE, HOLD, and DENY, wherein REQUIRE_OVERRIDE denotes that an explicit override indicator or attestation satisfying policy is required prior to finalization, and wherein enforcing the permit-before-finalization configuration comprises, responsive to the permit outcome corresponding to REQUIRE_OVERRIDE, withholding finalization absent the override indicator or attestation and, responsive to receiving the override indicator or attestation, permitting finalization by causing the policy evaluator to evaluate the policy graph with the override indicator or attestation as at least one of an additional input or an additional condition, thereby causing the policy evaluator to produce a permit outcome corresponding to the permit value for purposes of the user-interface finalization gate.

3. The bedside clinical device of claim 1, wherein the clinical context envelope further comprises at least one of: (i) a hashed or pseudonymized patient identifier; (ii) a modality identifier; or (iii) a timestamp or sequence identifier for the bedside inference episode.

4. The bedside clinical device of claim 1, wherein the policy graph encodes a condition that, when the attested device-state vector indicates that a power or temperature threshold is exceeded, causes the permit outcome to correspond to the non-permit value and thereby prevents finalization.

5. The bedside clinical device of claim 1, wherein enforcing the permit-before-finalization configuration further comprises: (i) in response to the permit outcome corresponding to the non-permit value, causing the user interface to render a safe-mode overlay in place of an AI output region; and (ii)

optionally allowing one or more non-AI device functions of the bedside clinical device to remain available.

6. The bedside clinical device of claim 1, wherein the plurality of enumerated outcomes further comprises a PERMIT_WITH_GUARDRAILS outcome that is a permit value, and wherein enforcing the permit-before-finalization configuration further comprises, when the permit outcome corresponds to the PERMIT_WITH_GUARDRAILS outcome, allowing finalization subject to at least one guardrail comprising suppressing at least one type of predicted value, risk score, or recommendation from being displayed or committed.

7. The bedside clinical device of claim 1, wherein generating the structured bedside safety receipt further comprises constructing a clinician response field indicating at least one of acceptance, override, or ignoring, and populating the clinician response field based on clinician actions captured via the user interface.

8. The bedside clinical device of claim 1, wherein generating the structured bedside safety receipt further comprises digitally signing the bedside safety receipt using a device key and anchoring at least a hash or commitment of the bedside safety receipt to an external tamper-evident store.

9. The bedside clinical device of claim 1, wherein the structured bedside safety receipt further encodes at least one of a finalization_gate_id or a ui_commit_scope identifier corresponding to the user-interface finalization gate at which finalization was allowed or prevented.

10. The bedside clinical device of claim 1, wherein obtaining the attested device-state vector further comprises verifying a remote attestation report from a trusted execution environment hosting the AI inference engine, and forcing the permit outcome to correspond to the non-permit value in response to a failure of the remote attestation report.

11. The bedside clinical device of claim 1, wherein the user-interface finalization gate comprises at least one of a display composition_layer, a display driver commit hook, a framebuffer commit boundary, a privileged user-interface service gateway, or an equivalent commit boundary at which output becomes user-visible or clinically actionable.

12. A computer-implemented method of governing bedside AI output finalization on a bedside clinical device, the method comprising:

(a) receiving, by a bedside AI permit rail executing on or adjacent to the bedside clinical device, at least one of an inference request or a user-interface finalization request for a bedside inference episode;

(b) obtaining, for the bedside clinical device, an attested device-state vector;

(c) obtaining, for the bedside inference episode, a clinical context envelope;

(d) obtaining a clinician identity token;

(e) evaluating a policy graph based at least on the attested device-state vector, the clinical context envelope, and the clinician identity token to compute a permit outcome selected from enumerated outcomes comprising at least a permit value and a non-permit value;

(f) enforcing a permit-before-finalization configuration by controlling a user interface at a user-interface finalization gate such that an AI inference output is prevented from being finalized to the user interface unless the permit outcome corresponds to the permit value; and (g) generating a structured bedside safety receipt encoding at least the attested device-state vector, the clinical context envelope, the clinician identity token, a policy identifier and at least one of a policy_version identifier, a policy digest, or a policy epoch associated with the policy graph, the permit outcome, and a summary or digest of the AI inference output.

13. The method of claim 12, wherein obtaining the attested device-state vector comprises sampling at least a battery state-of-charge indicator, a power source indicator, and a device temperature indicator.

14. The method of claim 12, further comprising rendering a safe-mode overlay in place of the AI inference output when the permit outcome corresponds to the non-permit value.

15. The method of claim 12, wherein the enumerated outcomes further comprise a PERMIT_WITH_GUARD-RAILS outcome that is a permit value, and wherein allowing finalization when the permit outcome corresponds to the PERMIT_WITH_GUARDRAILS outcome comprises suppressing at least one type of predicted value, risk score, or recommendation from being finalized to the user interface or stored.

16. The method of claim 12, wherein generating the structured bedside safety receipt further comprises capturing clinician actions and encoding a clinician response field.

17. The method of claim 12, further comprising digitally signing the structured bedside safety receipt and transmitting at least a hash or commitment of the structured bedside safety receipt to a tamper-evident store.

18. The method of claim 12, wherein generating the structured bedside safety receipt further comprises encoding at least one of a finalization_gate_id or a ui_commit_scope identifier corresponding to the user-interface finalization gate at which finalization was allowed or prevented.

19. A non-transitory computer-readable medium storing instructions that, when executed by one or more processors of a bedside clinical device, cause the bedside clinical device to perform the method of claim 12.

20. The non-transitory computer-readable medium of claim 19, wherein the instructions further cause the bedside clinical device to enforce the permit-before-finalization configuration at the user-interface finalization gate by preventing user-visible finalization of the AI inference output absent the permit outcome corresponding to the permit value.

* * * * *